(12) United States Patent
Toh

(10) Patent No.: US 6,256,647 B1
(45) Date of Patent: Jul. 3, 2001

(54) METHOD OF SEARCHING DATABASE OF THREE-DIMENSIONAL PROTEIN STRUCTURES

(75) Inventor: Hiroyuki Toh, Suita (JP)

(73) Assignee: Biomolecular Engineering Research Institute, Suita (JP)

( * ) Notice: Subject to any disclaimer, the term of this patent is extended or adjusted under 35 U.S.C. 154(b) by 0 days.

(21) Appl. No.: 09/250,730

(22) Filed: Feb. 16, 1999

(30) Foreign Application Priority Data

Feb. 16, 1998 (JP) .................................................. 10-032503

(51) Int. Cl.[7] .................................................. G06F 17/30
(52) U.S. Cl. .............................. 707/304; 707/4; 707/104; 435/69.1; 435/68.1; 702/22
(58) Field of Search .................................. 707/104, 3, 4; 435/69.1, 68.1, 106; 702/4, 22

(56) References Cited

U.S. PATENT DOCUMENTS

| | | | |
|---|---|---|---|
| 5,518,911 | * | 5/1996 | Abo et al. .............................. 435/194 |
| 5,752,019 | * | 5/1998 | Rigoutsos et al. ........................ 707/6 |
| 5,787,279 | * | 7/1998 | Rigoutsos et al. ........................ 707/3 |
| 5,824,490 | * | 10/1998 | Coffey et al. ......................... 435/7.23 |
| 5,878,373 | * | 3/1999 | Cohen et al. ........................... 702/22 |
| 5,884,230 | * | 3/1999 | Srinivasan et al. .................... 702/22 |
| 5,950,192 | * | 9/1999 | Moore et al. ............................. 707/3 |
| 6,048,706 | * | 4/2000 | Abo et al. .............................. 435/15 |
| 6,111,582 | * | 8/2000 | Jenkins ................................. 345/421 |
| 6,141,655 | * | 10/2000 | Johnson et al. .......................... 707/2 |

* cited by examiner

*Primary Examiner*—Jack Choules
*Assistant Examiner*—Debbie M. Le
(74) *Attorney, Agent, or Firm*—Oblon, Spivak, McClelland, Maier & Neustadt, P.C.

(57) ABSTRACT

A method of searching a database of three-dimensional protein structures. The method comprises the steps of setting a three-dimensional protein structure; forming a two-dimensional binary distance map based on the three-dimensional protein structure; forming a one-dimensional peripheral distribution based on the distance map; and comparing the one-dimensional peripheral distribution of a protein structure with that of another protein structure a dynamic programming algorithm. The method increases detection sensitivity and search speed.

7 Claims, 31 Drawing Sheets

SEQUENCE IDENTITY: 23.3%

SEQUENCE IDENTITY: 23.3%

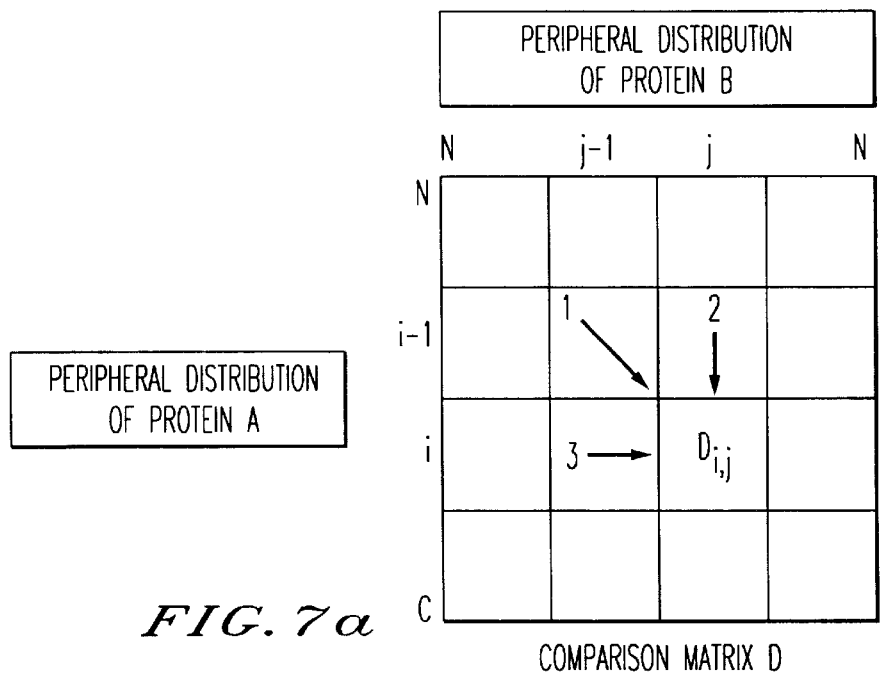

FIG. 7a

$$D_{i,j} = \max\{1\, D_{i-1,\, j-1} + S_{ij},\ 2\, D_{i-1,\, j} - g,\ 3\, D_{i,\, j-1} - g\}$$

$g = 5$ : GAP PENALTY (HOWEVER, $g = 0$ AT BOUNDARY)

$S_{ij}$ : SIMILARITY BETWEEN i-TH FREQUENCY OF PERIPHERAL DISTRIBUTION OF PROTEIN A AND j-TH FREQUENCY OF PERIPHERAL DISTRIBUTION OF PROTEIN B $$S_{ij} = a/\{(N^A_i - N^B_j)^2 + b\} + a/\{(C^A_i - C^B_j)^2 + b\}$$

$a = 50,\ b = 2$

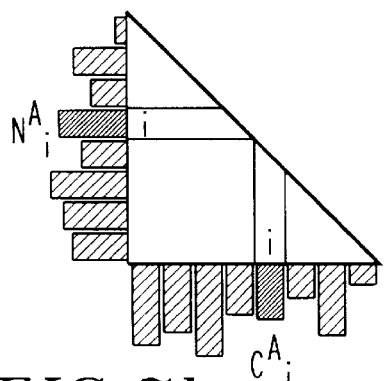

FIG. 7b

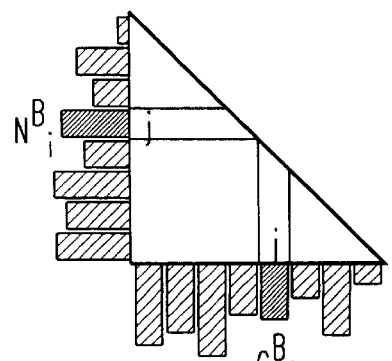

FIG. 7c

$N^A_i\,(C^A_i)$ : FREQUENCY OF PERIPHERAL DISTRIBUTION IN N (C) TERMINAL DIRECTION CORRESPONDING TO THE i-TH RESIDUE OF PROTEIN A

| PROTEIN | CODE | NUMBER OF RESIDUES |
|---|---|---|
| MAINLY α | | |
| 1. MYOGLOBIN | 1mbc | 153 |
| 2. CYTOCHROME C | 1ccr | 112 |
| 3. CYTOCHROME P450 | 1oxa | 403 |
| MAINLY β | | |
| 4. β-LACTOGLUBIN | 1beb (A CHAIN) | 162 |
| 5. TELOKIN-LIKE PROTEIN | 1tu1 | 108 |
| 6. INTERLEUKIN-1 β | 1i1b | 153 |
| α/β | | |
| 7. BIOTIN CARBOXYLASE | 1bnc | 449 |
| 8. HEAT-SHOCK PROTEIN 70kDa (HSP70) | 1atr | 386 |
| 9. THIOREDOXIN | 1ert | 105 |

*FIG. 8*

|  |  |  |
|---|---|---|
| 1th | pdb1atr.ent | HEAT-SHOCK COGNATE 70 KD PROTEIN (44 KD ATPASE N-TERMINAL (1) |
| 2th | pdb1ngf.ent | HEAT-SHOCK COGNATE 70KD PROTEIN (44KD ATPASE N-TERMINAL (1) |
| 3th | pdb1ngj.ent | HEAT-SHOCK COGNATE 70KD PROTEIN (44KD ATPASE N-TERMINAL (1) |
| 4th | pdb3hsc.ent | HEAT-SHOCK COGNATE 70KD PROTEIN (44KD ATPASW N-TERMINAL (1) |
| 5th | pdb1ats.ent | HEAT-SHOCK COGNATE 70 KD PROTEIN (44 KD ATPASE N-TERMINAL (1) |
| 6th | pdb1nga.ent | HEAT-SHOCK COGNATE 70KD PROTEIN (44KD ATPASE N-TERMINAL (1) |
| 7th | pdb1ngh.ent | HEAT-SHOCK COGNATE 70KD PROTEIN (44KD ATPASE N-TERMINAL (1) |
| 8th | pdb1ngg.ent | HEAT-SHOCK COGNATE 70KD PROTEIN (44KD ATPASE N-TERMINAL (1) |
| 9th | pdb1nge.ent | HEAT-SHOCK COGNATE 70KD PROTEIN (44KD ATPASE N-TERMINAL (1 |
| 10th | pdb1ngb.ent | HEAT-SHOCK COGNATE 70KD PROTEIN (44KD ATPASE N-TERMINAL (1) |
| 11th | pdb1ngi.ent | HEAT-SHOCK COGNATE 70KD PROTEIN (44KD ATPASE N-TERMINAL (1) |
| 12th | pdb1ngc.ent | HEAT-SHOCK COGNATE 70KD PROTEIN (44KD ATPASE N-TERMINAL (1) |
| 13th | pdb1ngd.ent | HEAT-SHOCK COGNATE 70KD PROTEIN (44KD ATPASE N-TERMINAL (1) |
| 14th | pdb1kax.ent | 70KD HEAT SHOCK COGNATE PROTEIN ATPASE DOMAIN, K71M MUTANT (1) |
| 15th | pdb1hpm.ent | 44K ATPASE FRAGMENT (N-TERMINAL) OF 70KDA HEAT-SHOCK COGNATE (1) |
| 16th | pdb1kay.ent | 70KD HEAT SHOCK COGNATE PROTEIN ATPASE DOMAIN, K71A MUTANT (1) |
| 17th | pdb1kaz.ent | 70KD HEAT SHOCK COGNATE PROTEIN ATPASE DOMAIN, K71E MUTANT (1) |
| 18th | pdb1atn.ent | DEOXYRIBONUCLEASE I COMPLEX WITH ACTIN (A) |

A — PROTEINS CLASSIFIED IN THE SAME FAMILY IN P I R

B — PROTEINS THAT ARE NOT CLASSIFIED IN THE SAME FAMILY IN P I R BUT CLASSIFIED IN THE SAME FAMILY IN S C O P

FIG. 10A

| | | |
|---|---|---|
| 19th | pdb2btf.ent | : BETA-ACTIN-PROFILIN COMPLEX (A) |
| 20th | pdb1glk.ent | : GLUCOKINASE (ATP:D-HEXOSE 6-PHOSPHOTRANSFERASE) (!) |
| 21st | pdb4gpd.ent | : APO-D-GYCERALDEHYDE-3-PHOSPHATE DEHYDROGENASE (3) |
| 22nd | pdb1tad.ent | : TRANSDUCIN-ALPHA (GT-ALPHA-GDF-ALF, T-ALPHA-GDP-ALF) (B) |
| 23rd | pdb1nlg.ent | : OXIDIZED NADF-LINKED GLYCERALDEHYDE-3-PHOSPHATE (!) |
| 24th | pdb1gga.ent | : D-GLYCERALDEHYDE-3-PHOSPHATE DEHYDROGENASE (HOLO FORM) (Q) |
| 25th | pdb4gpd.ent | : APO-D-GYCERALDEHYDE-3-PHOSPHATE DEHYDROGENASE (1) |
| 26th | pdb4gpd.ent | : APO-D-GYCERALDEHYDE-3-PHOSPHATE DEHYDROGENASE (4) |
| 27th | pdb4gpd.ent | : APO-D-GYCERALDEHYDE-3-PHOSPHATE DEHYDROGENASE (2) |
| 28th | pfn1pfk.ent | : PHOSPHOFRUCTOKINASE (E.C.2.7.1.11) (R-STATE) COMPLEX WITH (B) |
| 29th | pdb1gga.ent | : D-GLYCERALDEHYDE-3-PHOSPHATE DEHYDROGENASE (HOLO FORM) (P) |
| 30th | pdb1gga.ent | : D-GLYCERALDEHYDE-3-PHOSPHATE DEHYDROGENASE (HOLO FORM) (B) |
| 31st | pdb1hdg.ent | : HOLO-D-GLYCERALDEHYDE-3-PHOSPHATE DEHYDROGENASE (Q) |
| 32nd | pdb1gga.ent | : D-GLYCERALDEHYDE-3-PHOSPHATE DEHYDROGENASE (HOLO FORM) (A) |
| 33rd | pdb1gyp.ent | : MOLECULE: GLYCERALDEHYDE-3-PHOSPHATE DEHYDROGENASE (B) |
| 34th | pdb1gga.ent | : D-GLYCERALDEHYDE-3-PHOSPHATE DEHYDROGENASE (HOLO FORM) (D) |
| 35th | pdb1gyp.ent | : MOLECULE: GLYCERALDEHYDE-3-PHOSPHATE DEHYDROGENASE (A) |
| 36th | pdb1gyp.ent | : MOLECULE: GLYCERALDEHYDE-3-PHOSPHATE DEHYDROGENASE (C) |
| 37th | pdb1gga.ent | : D-GLYCERALDEHYDE-3-PHOSPHATE DEHYDROGENASE (HOLO FORM) (R) |

A : PROTEINS CLASSIFIED IN THE SAME FAMILY IN P I R

B : PROTEINS THAT ARE NOT CLASSIFIED IN THE SAME FAMILY IN P I R BUT CLASSIFIED IN THE SAME FAMILY IN S C O P

FIG. 10B

| | | |
|---|---|---|
| 38th | pdb1tad.ent : | TRANSDUCIN-ALPHA (GT-ALPHA-GDP-ALF, T-ALPHA-GDP-ALF) (A) |
| 39th | pdb1tag.ent : | TRANSDUCIN-ALPHA COMPLEXED WITH GDP AND MAGNESIUM (!) |
| 40th | pdb1gyp.ent : | MOLECULE: GLYCERALDEHYDE-3-PHOSPHATE DEHYDROGENASE; (D) |
| 41th | pdb1nlh.ent : | REDUCED NADP-LINKED GLYCERALDEHYDE-3-PHOSPHATE (!) |
| 42th | pdb1pfk.ent : | PHOSPHOFRUCTOKINASE (E.C.2.7.1.11) (R-STATE) COMPLEX WITH (A) |
| 43th | pdb1tad.ent : | TRANSDUCIN-ALPHA (GT-ALPHA-GDP-ALF, T-ALPHA-GDP-ALF) (C) |
| 44th | pdb1hdg.ent : | HOLO-D-GLYCERALDEHYDE-3-PHOSPHATE DEHYDROGENASE (O) |
| 45th | pdb1tnd.ent : | TRANSDUCIN (ALPHA SUBUNIT) COMPLEXED WITH THE (B) |
| 46th | pdb6pfk.ent : | PHOSPHOFRUCTOKINASE. INHIBITED T-STATE (C) |
| 47th | pdb1tnd.ent : | TRANSDUCIN (ALPHA SUBUNIT) COMPLEXED WITH THE (A) |
| 48th | pdb1cer.ent : | MOLECULE: HOLO-D-GLYCERALDEHYDE-3-PHOSPHATE DEHYDROGENASE: (P) |
| 49th | pdb1tdf.ent : | THIOREDOXIN REDUCTASE (E.C.1.6.4.5) MUTANT WITH CYS 138 (!) |
| 50th | pdb4dbv.ent : | GLYCERALDEHYDE-3-PHOSPHATE DEHYDROGENASE MUTANT WITH LEU 33 (D) |

| | |
|---|---|
| A | PROTEINS CLASSIFIED IN THE SAME FAMILY IN P I R |
| B | PROTEINS THAT ARE NOT CLASSIFIED IN THE SAME FAMILY IN P I R BUT CLASSIFIED IN THE SAME FAMILY IN S C O P |

*FIG. 10C*

| PROTEIN | R<0.12 | 0.12≤R≤0.16 | R<0.12 | FAMILY+SIMILAR STRUCTURE |
|---|---|---|---|---|
| MAINLY α | | | | |
| MYOGLOBIN (1mbc) | 324 + 0 | 329 + 0 | 329 + 0 | 329 + 6 |
| CYTOCHROME C (1ccr) | 44 + 0 | 53 + 0 | 52 + 0 | 72 + 0 |
| CYTOCHROME P450 (1oxa) | 31 + 0 | 31 + 0 | 31 + 0 | 31 + 0 |
| MAINLY β | | | | |
| β-LACTOGLOBULIN (1beb) | 25 + 0 | 25 + 25 | 25 + 1 | 25 + 71 |
| TELOKIN-LIKE PROTEIN (1tul) | 1 + 2 | 1 + 2 | 1 + 2 | 1 + 9 |
| INTERLEUKIN-1 β (1i1b) | 21 + 27 | 21 + 26 | 21 + 26 | 21 + 31 |
| α/β  α | | | | |
| BIOTIN CARBOXYLASE (1bnc) | 2 + 0 | 2 + 4 | 2 + 0 | 2 + 7 |
| HEAT-SHOCK PROTEIN 70kDa (1atr) | 17 + 2 | 17 + 2 | 17 + 2 | 17 + 2 |
| THIOREDOXIN (1ert) | 24 + 0 | 24 + 0 | 24 + 0 | 24 + 69 |

FIG. 11

| PROTEIN | MARGINAL DISTRIBUTION | DDP | FAMILY+SIMILAR STRUCTURE |
|---|---|---|---|
| MAINLY α | | | |
| MYOGLOBIN (1mbc) | 329 + 0 2.1h | 329 + 0 66.9h | 329 + 6 |
| CYTOCHROME C (1ccr) | 53 + 0 1.4h | 52 + 0 69.1h | 68 + 0 |
| CYTOCHROME P450 (1oxa) | 31 + 0 2.3h | – | 31 + 0 |
| MAINLY β | | | |
| β-LACTOGLOBULIN (1beb) | 25 + 25 1.4h | 25 + 0 72.8h | 25 + 71 |
| TELOKIN-LIKE PROTEIN (1tul) | 1 + 2 1.2h | – | 1 + 9 |
| INTERLEUKIN-1 β (1i1b) | 21 + 26 1.5h | – | 21 + 31 |
| α/β α | | | |
| BIOTIN CARBOXYLASE (1bnc) | 2 + 4 2.3h | – | 2 + 7 |
| HEAT-SHOCK PROTEIN 70kDa (1atr) | 17 + 2 2.9h | – | 17 + 2 |
| THIOREDOXIN (1ert) | 24 + 0 1.4h | – | 24 + 69 |

FIG. 12

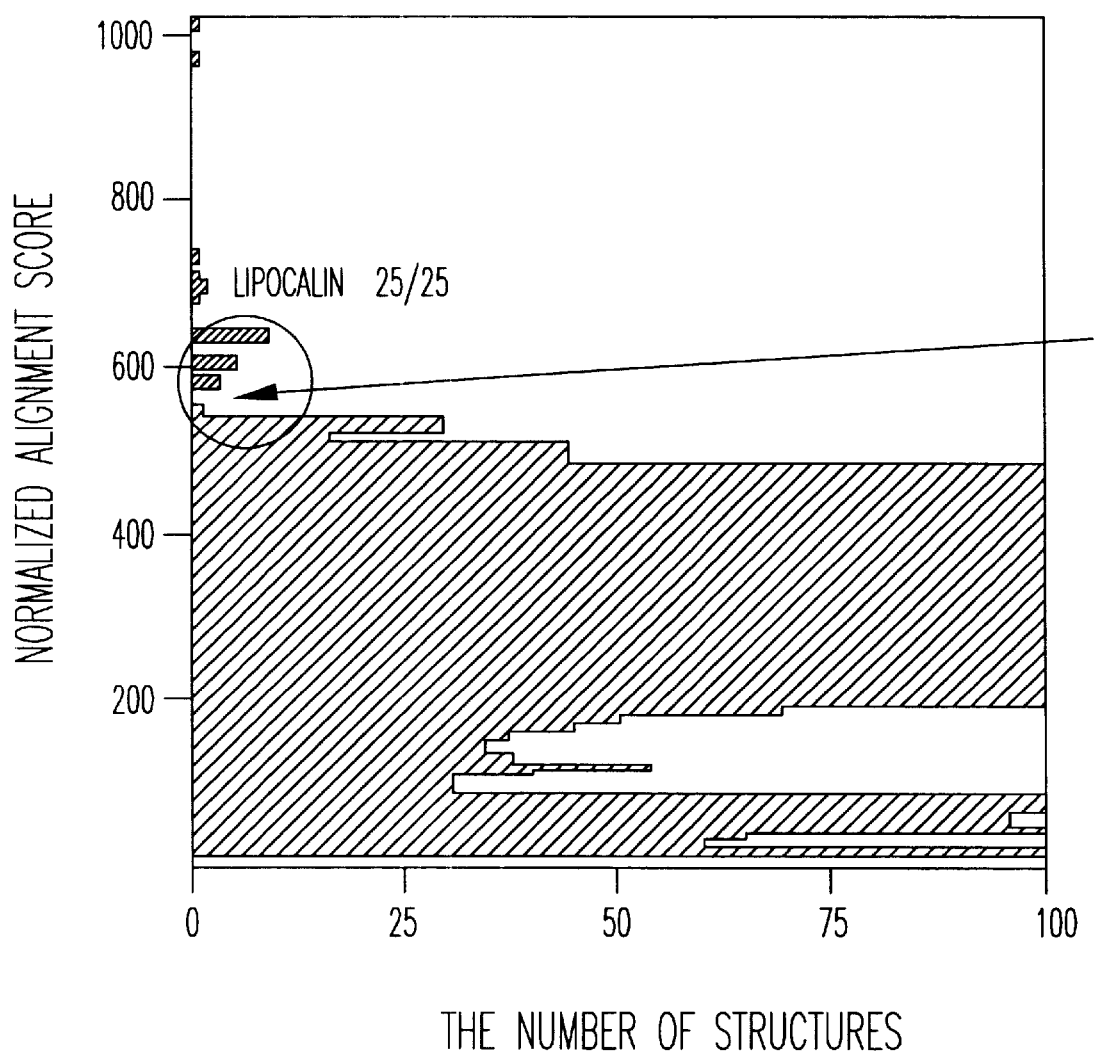
FIG. 13A.1

1th  pdb1beb.ent : LIPOCALIN (A)
2th  pdb1beb.ent : LIPOCALIN (B)
3th  pdb1mup.ent : PHEROMONE-BINDING (1)
4th  pdb1epa.ent : RETINOIC ACID-BINDING PROTEIN (B)
5th  pdb1epb.ent : RETINOIC ACID-BINDING PROTEIN (B)
6th  pdb1epa.ent : RETINOIC ACID-BINDING PROTEIN (A)
7th  pdb1epb.ent : RETINOIC ACID-BINGING PROTEIN (A)
8th  pdb1rbp.ent: RETINOL TRANSPORT (1)
9th  pdb1brq.ent : RETIONOL TRANSPORT (1)
10th pdb1hbp.ent : RETINOL TRANSPORT (1)
11th pdb1fem.ent : TRANSPORT PROTEIN (1)
12th pdb1erb.ent : RETINOL TRANSPORT (1)
13th pdb1fen.ent : TRANSPORT PROTEIN (1)
14th pdb1brp.ent : RETINOL TRANSPORT (1)
15th pdb1rlb.ent : COMPLEX (PROTEIN/PROTEIN) (E)
16th pdb1rlb.ent : COMPLEX (PROTEIN/PROTEIN) (F)
17th pdb1fel.ent : TRANSPORT PROTEIN (1)
18th pdb1hbq.ent : RETINOL TRANSPORT (1)
19th pdb1bbp.ent : BILIN BINDING (D)
20th pdb2apd.ent : LIPOCALIN (1)
21th pdb1bbp.ent : BILIN BINDING (C)
22th pdb1bbp.ent : BILIN BINGING (A)
23th pdb1bbp.ent : BILIN BINDING (B)
24th pdb1obp.ent : ODORANT-BINDING PROTEIN (B)
25th pdb1obp.ent : ODORANT-BINDING PROTEIN (A)
26th pdb1faj.ent : INORGANIC PYROPHOSPHATASE (1)
27th pdb2eip.ent : INORGANIC PYROPHOSPHATASE (A)
28th pdb1ums.ent : COMPLEX (PROTEINASE/INHIBITOR) (A)
29th pdb1igp.ent : ACID ANHYDRIDE HYDROLASE (1)
30th pdb1ino.ent : ACID ANHYDRIDE HYDROLASE (1)
31th pdb1rvv.ent : RIBOFLAVIN SYNTHASE (1)
32th pdb1rvv.ent : RIBOFLAVIN SYNTHASE (P)
33th pdb1rvv.ent : RIBOFLAVIN SYNTHASE (B)
34th pdb1rvv.ent : RIBOFLAVIN SYNTHASE (H)

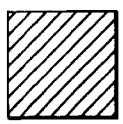  LIPOCALIN 25/25

  STREPTAVIDIN 0/33

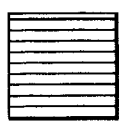  10-STRANDED β-BARREL 0/38

*FIG. 13A.2*

35th pdb1rvv.ent : RIBOFLAVIN SYNTHASE (U)
36th pdb1rvv.ent : RIBOFLAVIN SYNTHASE (X)
37th pdb1rvv.ent : RIBOFLAVIN SYNTHASE (W)
38th pdb1rvv.ent : RIBOFLAVIN SYNTHASE (F)
39th pdb1rvv.ent : RIBOFLAVIN SYNTHASE (C)
40th pdb1rvv.ent : RIBOFLAVIN SYNTHASE (L)
41th pdb1rvv.ent : RIBOFLAVIN SYNTHASE (A)
42th pdb1rvv.ent : RIBOFLAVIN SYNTHASE (O)
43th pdb1rvv.ent : RIBOFLAVIN SYNTHASE (Q)
44th pdb1rvv.etn : RIBOFLAVIN SYNTHASE (2)
45th pdb1rvv.ent : RIBOFLAVIN SYNTHASE (E)
46th pdb1rvv.ent : RIBOFLAVIN SYNTHASE (I)
47th pdb1rvv.ent : RIBOFLAVIN SYNTHASE (G)
48th pdb1rvv.ent : RIBOFLAVIN SYNTHASE (S)
49th pdb1rvv.ent : RIBOFLAVIN SYNTHASE (Z)
50th pdb1rvv.ent : RIBOFLAVIN SYNTHASE (3)

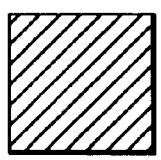  LIPOCALIN 25/25    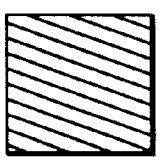  STREPTAVIDIN 0/33

  10-STRANDED β-BARREL 0/38

*FIG. 13A.3*

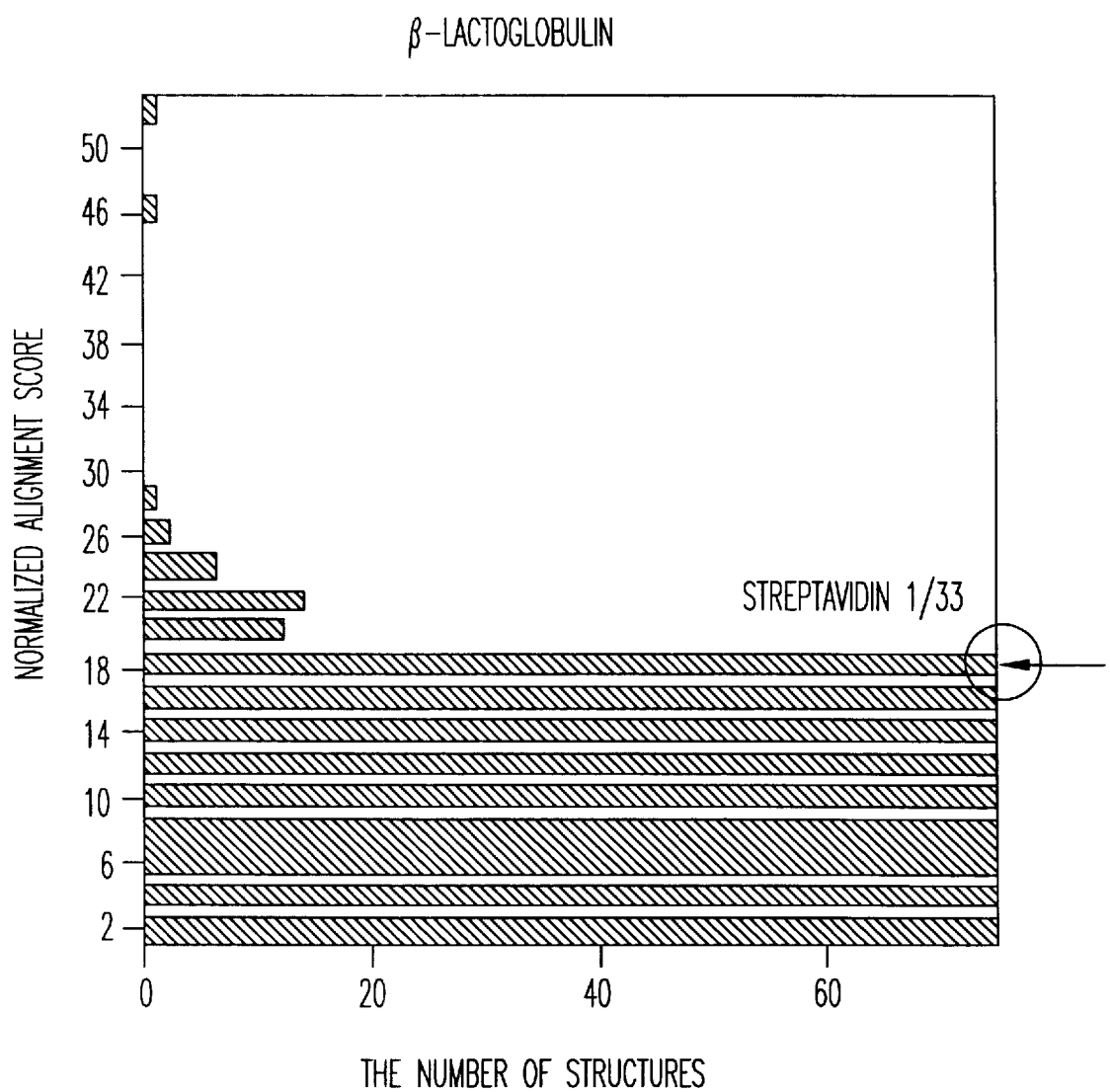
FIG. 13B.1

| | |
|---|---|
| 1th | pdb1beb.ent : BOVINE BETA-LACTOGLOBULIN, LATTICE X (A) |
| 2th | pdb1beb.ent : BOVINE BETA-LACTOGLOBULIN, LATTICE X (B) |
| 3th | pdb1mup.ent : MAJOR URINARY PROTEIN COMPLEX WITH 2-(SEC-BUTYL) (!) |
| 4th | pdb1epa.ent : EPIDIDYMAL RETINOIC ACID-BINDING PROTEIN (B) |
| 5th | pdb1epb.ent : EPIDIDYMAL RETINOIC ACID-BINDING PROTEIN (B) |
| 6th | pdb1epa.ent : EPIDIDYMAL RETINOIC ACID-BINDING PROTEIN (A) |
| 7th | pdb1epb.ent : EPIDIDYMAL RETINOIC ACID-BINDING PROTEIN (A) |
| 8th | pdb1obp.ent : ODORANT-BINDING PROTEIN FROM BOVINE NASAL MUCOSA (A) |
| 9th | pdb1rbp.ent : RETINOL BINDING PROTEIN (¡) |
| 10th | pdb1brq.ent : RETINOL BINDING PROTEIN (APO FORM) (!) |
| 11th | pdb1obp.ent : ODORANT-BINDING PROTEIN FROM BOVINE NASAL MUCOSA (B) |
| 12th | pdb1fem.ent : RETINOL BINDING PROTEIN COMPLEXED WITH RETINOIC ACID (!) |
| 13th | pdb1bbp.ent : BILIN BINDING PROTEIN (/BBP$) (C) |
| 14th | pdb1hbp.ent : RETINOL BINDING PROTEIN (HOLO FORM) (HOLO BRBP) (!) |
| 15th | pdb1bbp.ent : BILIN BINDING PROTEIN (/BBP$) (A) |
| 16th | pdb1fen.ent : RETINOL BINDING PROTEIN COMPLEXED WITH AXEROPHTHENE (!) |
| 17th | pdb1hbq.ent : RETINOL BINDING PROTEIN (APO FORM) (APO BRBP) (!) |
| 18th | pdb1bbp.ent : BILIN BINDING PROTEIN (/BBP$) (B) |
| 19th | pdb1bbp.ent : BILIN BINDING PROTEIN (/BBP$) (D) |
| 20th | pdb1rlb.ent : RETINOL BINDING PROTEIN COMPLEXED WITH TRANSTHYRETIN (E) |
| 21th | pdb1brp.ent : RETINOL BINDING PROTEIN (HOLO FORM) (!) |
| 22th | pdb1erb.ent : RETINOL BINDING PROTEIN COMPLEX WITH N-ETHYL RETINAMIDE (!) |
| 23th | pdb1rlb.ent : RETINOL BINDING PROTEIN COMPLEXED WITH TRANSTHYRETIN (F) |
| 24th | pdb2apd.ent : APOLIPOPROTEIN D (THEORETICAL MODEL) (!) |
| 25th | pdb1fel.ent : RETINOL BINDING PROTEIN COMPLEXED WITH FENRETINIDE (!) |
| 26th | pdb1abo.ent : C1G/V32D/F57H MUTANT OF MURINE ADIPOCYTE LIPID BINDING (!) |
| 27th | pdb1crb.ent : CELLULAR RETINOL BINDING PROTEIN (CRBP) COMPLEXED WITH (!) |
| 28th | pdb1acd.ent : V32D/F57H MUTANT OF MURINE ADIPOCYTE LIPID BINDING PROTEIN (!) |
| 29th | pdb1pmp.ent : P2 MYELIN PROTEIN (P2) (A) |
| 30th | pdb1cbi.ent : APO-CELLULAR RETINOIC ACID BINDING PROTEIN I (B) |
| 31th | pdb1lie.ent : ADIPOCYTE LIPID-BINDING PROTEIN COMPLEXED WITH PALMITIC ACID (!) |
| 32th | pdb1hms.ent : FATTY ACID BINDING PROTEIN (HUMAN MUSCLE, M-FABP) COMPLEXED (!) |
| 33th | pdb1cbq.ent : CELLULAR RETINOIC-ACID-BINDING PROTEIN TYPE II (!) |
| 34th | pdb1lic.ent : ADIPOCYTE LIPID-BINDING PROTEIN COMPLEXED WITH (!) |

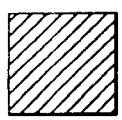 LIPOCALIN 25/25        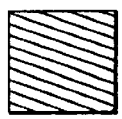 STREPTAVIDIN 1/33

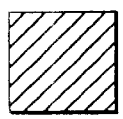 10-STRANDED β-BARREL 24/38

*FIG. 13B.2*

| | | |
|---|---|---|
| 35th | pdb1ifc.ent : | INTESTINAL FATTY ACID BINDING PROTEIN (APO FORM 2) (!) |
| 36th | pdb1ftp.ent : | FATTY-ACID-BINDING PROTEIN (B) |
| 37th | pdb1opb.ent : | CELLULAR RETINOL BINDING PROTEIN II (HOLO FORM) (D) |
| 38th | pdb1opb.ent : | CELLULAR RETINOL BINDING PROTEIN II (HOLO FORM) (C) |
| 39th | pdb1ftp.ent : | FATTY-ACID-BINDING PROTEIN (A) |
| 40th | pdb1cbs.ent : | CELLULAR RETINOIC-ACID-BINDING PROTEIN TYPE II COMPLEXED (!) |
| 41th | pdb1lif.ent : | ADIPOCYTE LIPID-BINDING PROTEIN COMPLEXED WITH STEARIC ACID (!) |
| 42th | pdb1opb.ent : | CELLULAR RETINOL BINDING PROTEIN II (HOLO FORM) (B) |
| 43th | pdb1hmt.ent : | FATTY ACID BINDING PROTEIN (HUMAN MUSCLE, M-FABP) COMPLEXED (!) |
| 44th | pdb1lib.ent : | ADIPOCYTE LIPID-BINDING PROTEIN (!) |
| 45th | pdb1pmp.ent : | P2 MYELIN PROTEIN (P2) (C) |
| 46th | pdb1opa.ent : | CELLULAR RETINOL BINDING PROTEIN II (APO FORM) (APO-CRBPII) (A) |
| 47th | pdb1ifb.ent : | INTESTINAL FATTY ACID BINDING PROTEIN (APO FORM 1) (!) |
| 48th | pdb1mdc.ent : | FATTY ACID BINDING PROTEIN (MANDUCA SEXTA) (MFB2) (!) |
| 49th | pdb1adl.ent : | ADIPOCYTE LIPID-BINDING PROTEIN COMPLEXED WITH ARACHIDONIC (!) |
| 50th | pdb1pts.ent : | STREPTAVIDIN COMPLEX WITH THE PEPTIDE (FSHPQNT) (A) |

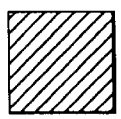 LIPOCALIN 25/25

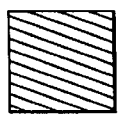 STREPTAVIDIN 1/33

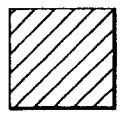 10-STRANDED β-BARREL 24/38

*FIG. 13B.3*

```
HSP70   <20   151   0:  ─────
        22      0   0:    ONE -- REPRESNETS 1 LIBRARY SEQUENCES
FASTA   24      2   0: ─
        26      1   0: ─
        28      9   2: *
        30     17  13: *─
        32    104  49: ─*─
        34    244 133: ─────*──────
        36    268 273: ──────────────*
        38    389 452: ─────────────────────*
        40    643 630: ─────────────────────────────*─
        42    622 770: ──────────────────────────────────  *
        44    790 850: ────────────────────────────────────*
        46    915 865: ──────────────────────────────────────*
        48    733 828: ───────────────────────────────────  *
        50    650 756: ───────────────────────────────  *
        52    557 665: ───────────────────────────  *
        54    797 568: ───────────────────────*─────
        56    648 474: ───────────────────*
        58    391 389: ────────────────*
        60    352 315: ─────────────*─
        62    201 253: ──────────*
        64    150 201: ────────*
        66    186 159: ──────*─
        68     33 125: ────*
        70    129  98: ───*─
        72    131  77: ──*──
        74     35  60: ─*
        76     43  46: ─*
        78     18  36: ─*
        80     10  28: ─*
        82     34  21: ─*─
        84     59  17: ─*─
        86      5  13: *       INSET -- REPRESNETS 1 LIBRARY SEQUENCES
        88     16  10: *
        90      8   8: *
        92      5   6: *   :───*
        94      7   5: *   :──*─
        96      5   4: *   :─*─
        98      3   3: *   :─*
       100      2   2: *   :─*
       102      0   2: *   :*
       104      0   1: *   :*
       106      0   1: *   :*
       108      2   1: *   :*─
       110      0   1: *   :*
       112      0   0:    *
       114      0   0:    *
       116      0   0:    *
       118      0   0:    *
       >>120   17   0: ─   *────────
```

FIG. 14A.1

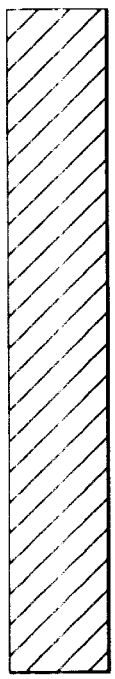

```
str:1ATR  HEAT-SHOCK COGNATE 70KD PROTEIN (386) 2470 2470 2470 2938.7 0
str:1NGI  HEAT-SHOCK COGNATE 70KD PROTEIN (386) 2465 2465 2465 2932.8 0
str:3HSC  HEAT-SHOCK COGNATE 70KD PROTEIN (386) 2465 2465 2465 2932.8 0
str:1HPM  44K ATPASE FRAGMENT (N-TERMINAL (386) 2465 2465 2465 2932.8 0
str:1NGJ  HEAT-SHOCK COGNATE 70KD PROTEIN (386) 2465 2465 2465 2932.8 0
str:1ATS  HEAT-SHOCK COGNATE 70KD PROTEIN (386) 2462 2462 2462 2929.2 0
str:1NGB  HEAT-SHOCK COGNATE 70KD PROTEIN (386) 2461 2461 2461 2928.0 0
str:1NGF  HEAT-SHOCK COGNATE 70KD PROTEIN (386) 2459 2459 2459 2925.6 0
str:1NGD  HEAT-SHOCK COGNATE 70KD PROTEIN (386) 2459 2459 2459 2925.6 0
str:1NGH  HEAT-SHOCK COGNATE 70KD PROTEIN (386) 2459 2459 2459 2925.6 0
str:1NGA  HEAT-SHOCK COGNATE 70KD PROTEIN (386) 2458 2458 2458 2924.4 0
str:1NGE  HEAT-SHOCK COGNATE 70KD PROTEIN (386) 2457 2457 2457 2923.2 0
str:1NGC  HEAT-SHOCK COGNATE 70KD PROTEIN (386) 2457 2457 2457 2923.2 0
str:1NGG  HEAT-SHOCK COGNATE 70KD PROTEIN (386) 2457 2457 2457 2923.2 0
str:1KAZ  70KD HEAT SHOCK COGNATE PROTEIN (381) 2427 2427 2427 2887.6 0
str:1KAY  70KD HEAT SHOCK COGNATE PROTEIN (381) 2425 2425 2425 2885.2 0
str:1KAX  70KD HEAT SHOCK COGNATE PROTEIN (381) 2424 2424 2424 2884.0 0
str:1IEBB HISTOCOMPATIBILITY ANTIGEN MOL (227)  92   92   92  108.0 3
str:1IEBD HISTOCOMPATIBILITY ANTIGEN MOL (227)  92   92   92  108.0 3
str:1ZYMA AMINO TERMINAL DOMAIN OF ENZYM (258)  82   82   86   99.7 8.8
str:1ZYMB AMINO TERMINAL DOMAIN OF ENZYM (258)  82   82   86   99.7 8.8
str:1YTJA SIV PROTEASE CRYSTALLIZED WITH ( 99)  39   39   78   98.9 9.8
str:1YTIA SIV PROTEASE CRYSTALLIZED WITH ( 99)  39   39   78   98.9 9.8
```

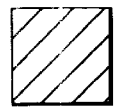 HSP70  17/17

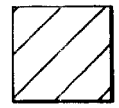 ACTIN  0/2

*FIG. 14A.2*

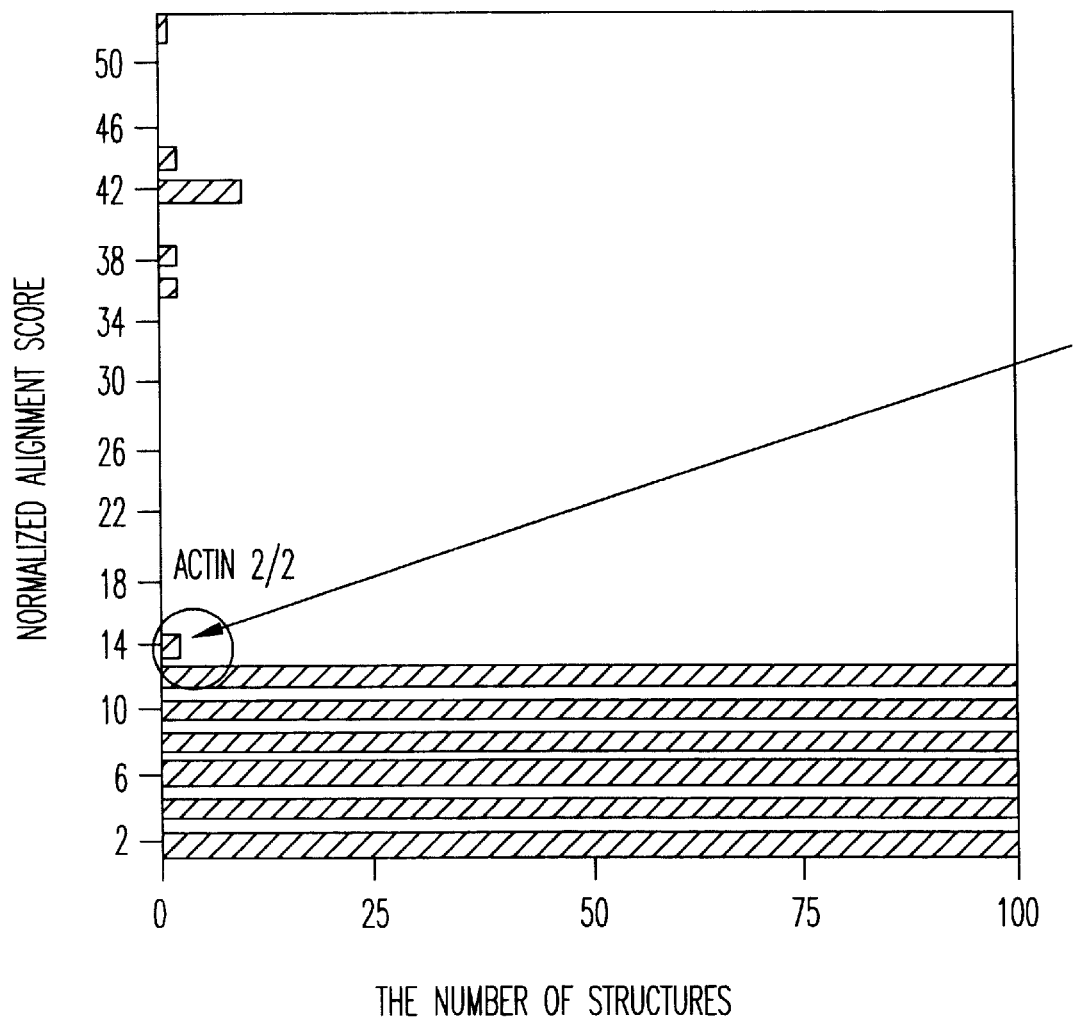
FIG. 14B.1

| | | |
|---|---|---|
| 1th | pdb1atr.ent : | HEAT-SHOCK COGNATE 70KD PROTEIN (44KD ATPASE N-TERMINAL (!) |
| 2th | pdb1ngf.ent : | HEAT-SHOCK COGNATE 70KD PROTEIN (44KD ATPASE N-TERMINAL (!) |
| 3th | pdb1ngj.ent : | HEAT-SHOCK COGNATE 70KD PROTEIN (44KD ATPASE N-TERMINAL (!) |
| 4th | pdb3hsc.ent : | HEAT-SHOCK COGNATE 70DK PROTEIN (44KD ATPASE N-TERMINAL (!) |
| 5th | pdb1ats.ent : | HEAT-SHOCK COGNATE 70KD PROTEIN (44KD ATPASE N-TERMINAL (!) |
| 6th | pdb1nga.ent : | HEAT-SHOCK COGNATE 70KD PROTEIN (44KD ATPASE N-TERMINAL (!) |
| 7th | pdb1ngh.ent : | HEAT-SHOCK COGNATE 70KD PROTEIN (44KD ATPASE N-TERMINAL (!) |
| 8th | pdb1ngg.ent : | HEAT-SHOCK COGNATE 70KD PROTEIN (44KD ATPASE N-TERMINAL (!) |
| 9th | pdb1nge.ent : | HEAT-SHOCK COGNATE 70KD PROTEIN (44KD ATPASE N-TERMINAL (!) |
| 10th | pdb1ngb.ent : | HEAT-SHOCK COGNATE 70KD PROTEIN (44KD ATPASE N-TERMINAL (!) |
| 11th | pdb1ngi.ent : | HEAT-SHOCK COGNATE 70KD PROTEIN (44KD ATPASE N-TERMINAL (!) |
| 12th | pdb1ngc.ent : | HEAT-SHOCK COGNATE 70KD PROTEIN (44KD ATPASE N-TERMINAL (!) |
| 13th | pdb1ngd.ent : | HEAT-SHOCK COGNATE 70KD PROTEIN (44KD ATPASE N-TERMINAL (!) |
| 14th | pdb1kax.ent : | 70KD HEAT SHOCK COGNATE PROTEIN ATPASE DOMAIN, K71M MUTANT (!) |
| 15th | pdb1hpm.ent : | 44K ATPASE FRAGMENT (N-TERMINAL) OF 70KDA HEAT-SHOCK COGNATE (!) |
| 16th | pdb1kay.ent : | 70KD HEAT SHOCK COGNATE PROTEIN ATPASE DOMAIN, K71A MUTANT (!) |
| 17th | pdb1kaz.ent : | 70KD HEAT SHOCK COGNATE PROTEIN ATPASE DOMAIN, K71E MUTANT (!) |
| 18th | pdb1atn.ent : | DEOXYRIBONUCLEASE I COMPLEX WITH ACTIN (A) |
| 19th | pdb2btf.ent : | BETA-ACTIN-PROFILIN COMPLEX (A) |
| 20th | pdb1glk.ent : | GLUCOKINASE (ATP:D-HEXOSE 6-PHOSPHOTRANSFERASE) (!) |
| 21th | pdb4gpd.ent : | APO-D-GYCERALDEHYDE-3-PHOSPHATE DEHYDROGENASE (3) |
| 22th | pdb1tad.ent : | TRANSDUCIN-ALPHA (GT-ALPHA-GDP-ALF, T-ALPHA-GDP-ALF) (B) |
| 23th | pdb1nlg.ent : | OXIDIZED NADP-LINKED GLYCERALDEHYDE-3-PHOSPHATE (!) |
| 24th | pdb1gga.ent : | D-GLYCERALDEHYDE-3-PHOSPHATE DEHYDROGENASE (HOLO FORM) (Q) |
| 25th | pdb4gpd.ent : | APO-D-GYCERALDEHYDE-3-PHOSPHATE DEHYDROGENASE (!) |
| 26th | pdb4gpd.ent : | APO-D-GYCERALDEHYDE-3-PHOSPHATE DEHYDROGENASE (4) |
| 27th | pdb4gpd.ent : | APO-D-GYCERALDEHYDE-3-PHOSPHATE DEHYDROGENASE (2) |
| 28th | pdb1pfk.ent : | PHOSPHOFRUCTOKINASE (E.C.2.7.1.11) (R-STATE) COMPLEX WITH (B) |
| 29th | pdb1gga.ent : | D-GLYCERALDEHYDE-3-PHOSPHATE DEHYDROGENASE (HOLO FORM) (P) |
| 30th | pdb1gga.ent : | D-GLYCERALDEHYDE-3-PHOSPHATE DEHYDROGENASE (HOLO FORM) (B) |
| 31th | pdb1hdg.ent : | HOLO-D-GLYCERALDEHYDE-3-PHOSPHATE DEHYDROGENASE (Q) |
| 32th | pdb1gga.ent : | D-GLYCERALDEHYDE-3-PHOSPHATE DEHYDROGENASE (HOLO FORM) (A) |
| 33th | pdb1gyp.ent : | MOLECULE: GLYCERALDEHYDE-3-PHOSPHATE DEHYDROGENAS; (B) |
| 34th | pdb1gga.ent : | D-GLYCERALDEHYDE-3-PHOSPHATE DEHYDROGENASE (HOLO FORM) (O) |

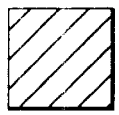 HSP70 17/17

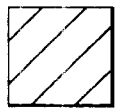 ACTIN 2/2

*FIG. 14B.2*

35th pdb1gyp.ent : MOLECULE: GLYCERALDEHYDE-3-PHOSPHATE DEHYDROGENASE; (A)
36th pdb1gyp.ent : MOLECULE: GLYCERALDEHYDE-3-PHOSPHATE DEHYDROGENASE; (C)
37th pdb1gga.ent : D-GLYCERALDEHYDE-3-PHOSPHATE DEHYDROGENASE (HOLO FORM) (R)
38th pdb1tad.ent : TRANSDUCIN-ALPHA (GT-ALPHA-GDP-ALF, T-ALPHA-GDP-ALF) (A)
39th pdb1tag.ent : TRANSDUCIN-ALPHA COMPLEXED WITH GDP AND MAGNESIUM (!)
40th pdb1gyp.ent : MOLECULE: GLYCERALDEHYDE-3-PHOSPHATE DEHYDROGENASE; (D)
41th pdb1nlh.ent : REDUCED NADP-LINKED GLYCERALDEHYDE-3-PHOSPHATE (!)
42th pdb1pfk.ent : PHOSPHOFRUCTOKINASE (E.C.2.7.1.11) (R-STATE) COMPLEX WITH (A)
43th pdb1tad.ent : TRANSDUCIN-ALPHA (GT-ALPHA-GDP-ALF, T-ALPHA-GDP-ALF) (C)
44th pdb1hdg.ent : HOLO-D-GLYCERALDEHYDE-3-PHOSPHATE DEHYDROGENASE (O)
45th pdb1tnd.ent : TRANSDUCIN (ALPHA SUBUNIT) COMPLEXED WITH THE (B)
46th pdb6pfk.ent : PHOSPHOFRUCTOKINASE, INHIBITED T-STATE (C)
47th pdb1tnd.ent : TRANSDUCIN (ALPHA SUBUNIT) COMPLEXED WITH THE (A)
48th pdb1cer.ent : MOLECULE: HOLO-D-GLYCERALDEHYDE-3-PHOSPHATE DEHYDROGENASE; (P)
49th pdb1tdf.ent : THIOREDOXIN REDUCTASE (E.C.1.6.4.5) MUTANT WITH CYS 138 (!)
50th pdb4dbv.ent : GLYCERALDEHYDE-3-PHOSPHATE DEHYDROGENASE MUTANT WITH LEU 33 (O)

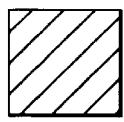 HSP70 17/17

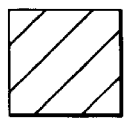 ACTIN 2/2

*FIG. 14B.3*

```
*BIOTIN CARBOXYLASE  <20  153    0>:————
 FASTA                22    0    0:     ONE = REPRESENTS 17 LIBRARY SEQUENCES
                      24    0    0:
                      26    1    0:-
                      28    0    2:*
                      30   21   13:*—
                      32  112   49:———*———
                      34  252  133:——————*———
                      36  338  274:————————————*——
                      38  420  452:————————————————*
                      40  511  631:———————————————————*
                      42  525  771:———————————————————————*
                      44  742  851:——————————————————————————*
                      46  812  866:—————————————————————————————*
                      48  965  830:——————————————————————————————*———
                      50  688  757:————————————————————————————*
                      52  523  665:————————————————————————*
                      54  592  568:———————————————————*—
                      56  465  475:——————————————————*
                      58  475  390:—————————————*———
                      60  403  316:——————————*———
                      62  208  253:————————*
                      64  214  201:——————*—
                      66  207  159:—————*—
                      68  109  125:————*
                      70  153   98:——*—
                      72   82   77:—*
                      74   94   60:—*—
                      76   69   47:—*—
                      78   44   36:—*
                      80   54   28:-*—
                      82   57   21:-*—
                      84   10   17:*
                      86    9   13:*
                      88   13   10:*      INSET = REPRESENTS 1 LIBRARY SEQUENCES
                      90   10    8:*
                      92   12    6:*      ———*———
                      94    3    5:*      — *
                      96    5    4:*      —*-
                      98    5    3:*      —*—
                     100    0    2:*      :*
                     102    1    2:*      :-*
                     104    0    1:*      :*
                     106   20    1:*—     :
                     108    0    1:*      :*
                     110    0    1:*      :*
                     112    0    0:       *
                     114    0    0:       *
                     116    0    0:       *
                     118    0    0:       *
                    >>120    5    0:      *  ———
```

*FIG. 15A.1*

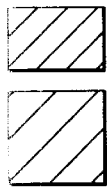
str:1BNCA MOL_ID: 1; MOLECULE:BIOTIN CA ( 449) 2973 2973 2973 4060.0 0
str:1BNCB MOL_ID: 1; MOLECULE:BIOTIN CA ( 449) 2973 2973 2973 4060.0 0
str:2DLN MOL_ID: 1; MOLECULE: D-ALANINE- ( 306) 148 73 163 210.3 6.1e-06
str:1IOV COMPLEX OF D-ALA:D-ALAIGASE W ( 306) 148 73 163 210.3 6.1e-06
str;1IOW COMPLEX OF Y216F D-ALA:D-ALA LI ( 306) 148 73 161 207.6 8.6e-06
str:1MAT METHIONINE AMINOPEPTIDASE (E.C. ( 264) 54 54 86 106.2 3.8
str:1CP4 CYTOCHROME P450=CAM=(CAMPHOR M ( 414) 41 41 89 105.8 4
str:4CPP CYTOCHROME P450CAM (CAMPHOR MON ( 414) 41 41 89 105.8 4
str:3CPP CYTOCHROME P450CAM (CAMPHOR MON ( 414) 41 41 89 105.8 4
str:1PHG CYTOCHROME P450-CAM (E.C.1.14.1 ( 414) 41 41 89 105.8 4
str:8CPP CYTOCHROME P450CAM (CAMPHOR MON ( 414) 41 41 89 105.8 4
str:7CPP CYTOCHROME P450CAM (CAMPHOR MON ( 414) 41 41 89 105.8 4
str:5CPP CYTOCHROME P450CAM (CAMPHOR MON ( 414) 41 41 89 105.8 4
str:1PHE CYTOCHROME P450-CAM (E.C.1.14.1 ( 414) 41 41 89 105.8 4
str:1PHF CYTOCHROME P450-CAM (E.C.1.14.1 ( 414) 41 41 89 105.8 4
str:1NOO CYTOCHROME P450CAM COMPLEXED WI ( 414) 41 41 89 105.8 4
str:2CP4 CYTOCHROME P450CAM (CAMPHOR MON ( 414) 41 41 89 105.8 4
str:4CP4 CYTOCHROME P450CAM (CAMPHOR MON ( 414) 41 41 89 105.8 4
str:3CP4 CYTOCHROME P450CAM (CAMPHOR MON ( 414) 41 41 89 105.8 4
str:1PHB CYTOCHROME P450-CAM (E.C.1.14.1 ( 414) 41 41 89 105.8 4
str:1PHC CYTOCHROME P450-CAM (E.C.1.14.1 ( 414) 41 41 89 105.8 4
str:1PHD CYTOCHROME P450-CAM (E.C.1.14.1 ( 414) 41 41 89 105.8 4
str:6CPP CYTOCHROME P450CAM (CAMPHOR MON ( 414) 41 41 89 105.8 4
str:2CPP CYTOCHROME P450CAM (CAMPHOR MON ( 414) 41 41 89 105.8 4
str:1PHA CYTOCHROME P450-CAM (E.C.1.14.1 ( 414) 41 41 89 105.8 4
str:1THG LIPASE (E.C.3.1.1.3)TRIACYGLY ( 544) 61 61 88 101.7 6.8

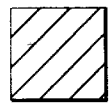 BIOTIN CARBOXYLASE 2/2    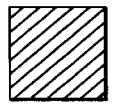 GLUTATHIONE SYNTHETASE 0/4

 D-ALA--- D-ALA LIGASE 3/3

*FIG. 15A.2*

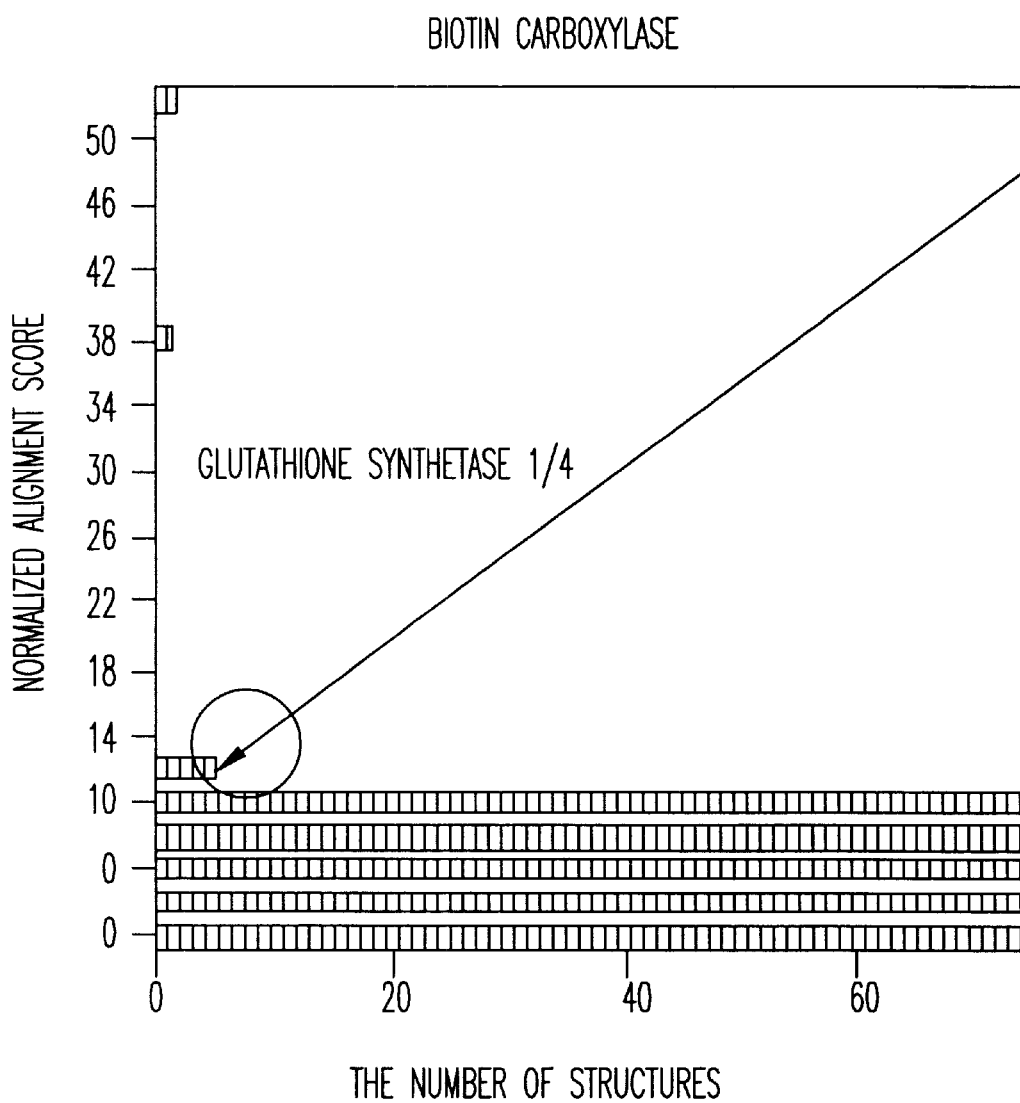
FIG. 15B.1

| | 1th | pdb1bnc.ent : | MOLECULE: BIOTIN CARBOXYLASE; (A) |
|---|---|---|---|
| | 2th | pdb1bnc.ent : | MOLECULE: BIOTIN CARBOXYLASE; (B) |
| | 3th | pdb1iow.ent : | COMPLEX OF Y216F D-ALA:D-ALA LIGASE WITH ADP AND A (!) |
| | 4th | pdb2dln.ent : | MOLECULE: D-ALANINE--D-ALANINE LIGASE; (!) |
| | 5th | pdb1iov.ent : | COMPLEX OF D-ALA:D-ALA LIGASE WITH ADP AND A PHOSPHORYL (!) |
| | 6th | pdb1gsh.ent : | STRUCTURE OF ESCHERICHIA COLI GLUTATHIONE SYNTHETASE AT PH (!) |
| | 7th | pdb1psd.ent : | D-3-PHOSPHOGLYCERATE DEHYDROGENASE (PHOSPHOGLYCERATE (A) |
| | 8th | pdb1gsa.ent : | STRUCTURE OF GLUTATHIONE SYNTHETASE COMPLEXED WITH ADP AND (!) |
| | 9th | pdb1psd.ent : | D-3-PHOSPHOGLYCERATE DEHYDROGENASE (PHOSPHOGLYCERATE (B) |
| | 10th | pdb1wip.ent : | STRUCTURE OF T-CELL SURFACE GLYCOPROTEIN CD4, MONOCLINIC (A) |
| | 11th | pdb1ecl.ent : | AMINO TERMINAL 67KDA DOMAIN OF ESCHERICHIA COLI DNA (!) |
| | 12th | pdb1sft.ent : | ALANINE RACEMASE (A) |
| | 13th | pdb1anw.ent : | ANNEXIN V (B) |
| | 14th | pdb2glt.ent : | STRUCTURE OF ESCHERICHIA COLI GLUTATHIONE SYNTHETASE AT PH (!) |
| | 15th | pdb1fcd.ent : | FLAVOCYTOCHROME C SULFIDE DEHYDROGENASE (FCSD) (A) |
| | 16th | pdb1sft.ent : | ALANINE RACEMASE (B) |
| | 17th | pdb1wiq.ent : | STRUCTURE OF T-CELL SURFACE GLYCOPROTEIN CD4, TRIGONAL (A) |
| | 18th | pdb1fcd.ent : | FLAVOCYTOCHROME C SULFIDE DEHYDROGENASE (FCSD) (B) |
| | 19th | pdb1fnf.ent : | FRAGMENT OF HUMAN FIBRONECTIN ENCOMPASSING TYPE-III (!) |
| | 20th | pdb1wip.ent : | STRUCTURE OF T-CELL SURFACE GLYCOPROTEIN CD4, MONOCLINIC (B) |
| | 21th | pdb1avr.ent : | ANNEXIN V (RHOMOBOHEDRAL CRYSTAL FORM) (!) |
| | 22th | pdb1wio.ent : | STRUCTURE OF T-CELL SURFACE GLYCOPROTEIN CD4, TETRAGONAL (B) |
| | 23th | pdb1pgn.ent : | 6-PHOSPHOGLUCONATE DEHYDROGENASE (6-PGDH) (E.C.1.1.1.44) (!) |
| | 24th | pdb1pbd.ent : | P-HYDROXYBENZOATE HYDROXYLASE (PHBH) (E.C.1.14.13.2) MUTANT (!) |
| | 25th | pdb3dbv.ent : | GLYCERALDEHYDE-3-PHOSPHATE DEHYDROGENASE MUTANT WITH LEU 33 (P) |
| | 26th | pdb1ala.ent : | ANNEXIN V (!) |
| | 27th | pdb1eps.ent : | 5-ENOL-PYRUVYL-3-PHOSPHATE SYNTHASE (E.C.2.5.1.9) (!) |
| | 28th | pdb4dbv.ent : | GLYCERALDEHYDE-3-PHOSPHATE DEHYDROGENASE MUTANT WITH LEU 33 |
| | 29th | pdb1wio.ent : | STRUCTURE OF T-CELL SURFACE GLYCOPROTEIN CD4, TETRAGONAL (A) |
| | 30th | pdb1anx.ent : | ANNEXIN V (C) |
| | 31th | pdb1ann.ent : | ANNEXIN IV (!) |
| | 32th | pdb1crk.ent : | MITOCHONDRIAL CREATINE KINASE (A) |
| | 33th | pdb1dbv.ent : | GLYCERALDEHYDE-3-PHOSPHATE DEHYDROGENASE MUTANT WITH ASP 32 (R) |
| | 34th | pdb1npx.ent : | NADH PEROXIDASE (E.C.1.11.1.1) NON-ACTIVE FORM WITH (!) |

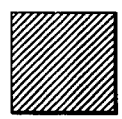 BIOTIN CARBOXYLASE 2/2

 GLUTATHIONE SYNTHETASE 1/4

*FIG. 15B.2*

35th pdb1rba.ent : RUBISCO (RIBULOSE-1,5-BISPHOSPHATE CARBOXYLASE/OXYGENASE) (B)
36th pdb1hvd.ent : ANNEXIN V (LIPOCORTIN V, ENDONEXIN II, PLACENTAL (!)
37th pdb1geo.ent : SULFITE REDUCTASE STRUCTURE AT 1.6 ANGSTROM RESOLUTION (!)
38th pdb1hvg.ent : ANNEXIN V (LIPOCORTIN V, ENDONEXIN II, PLACENTAL (!)
39th pdb1gyp.ent :   MOLECULE: GLYCERALDEHYDE-3-PHOSPHATE DEHYDROGENASE; (C)
40th pdb1gdl.ent : $HOLO-*D-*GLYCERALDEHYDE-3-PHOSPHATE DEHYDROGENASE (Q)
41th pdb1glv.ent : GLUTATHIONE SYNTHASE (E.C.6.3.2.3) LOOPLESS MUTANT WITH (!)
42th pdb4icd.ent : PHOSPHORYLATED ISOCITRATE DEHYDROGENASE (E.C.1.1.1.42) (!)
43th pdb1dnp.ent : STRUCTURE OF DEOXYRIBODIPYRIMIDINE PHOTOLYASE (A)
44th pdb1gga.ent : D-GLYCERALDEHYDE-3-PHOSPHATE DEHYDROGENASE (HOLO FORM) (P)
45th pdb1rld.ent : RIBULOSE-1,5-BISPHOSPHATE CARBOXYLASE/OXYGENASE (RUBISCO) (B)
46th pdb1pgp.ent : 6-PHOSPHOGLUCONATE DEHYDROGENASE (6-PGDH) (E.C.1.1.1.44) (!)
47th pdb1hop.ent : STRUCTURE OF GUANINE NUCLEOTIDE (GPPCP) COMPLEX OF (B)
48th pdb1iso.ent : ISOCITRATE DEHYDROGENASE: STRUCTURE OF AN ENGINEERED (!)
49th pdb1avh.ent : ANNEXIN V (HEXAGONAL CRYSTAL FORM) (A)
50th pdb1dnp.ent : STRUCTURE OF DEOXYRIBODIPYRIMIDINE PHOTOLYASE (B)

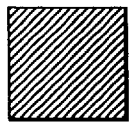 BIOTIN CARBOXYLASE 2/2

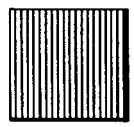 GLUTATHIONE SYSTHETASE 1/4

*FIG. 15B.3*

METHOD OF SEARCHING DATABASE OF THREE-DIMENSIONAL PROTEIN STRUCTURES

BACKGROUND OF THE INVENTION

1. Field of the Invention

The present invention relates to a method of searching a database of three-dimensional protein structures (hereinafter simply referred to as a "protein structure database"), and particularly to a method of searching a protein structure database through use of peripheral distributions of distance maps.

2. Description of the Related Art

The three-dimensional structure of a protein provides various kinds of information in terms of pharmacology and physical chemistry, as well as important information in terms of biology. With recent progress in structure determination techniques, the number of entries in a protein structure database has increased drastically. One technique for analyzing proteins is comparison analysis in which similar structures are compared to each other. Comparative analysis requires a technique for searching a structure database of huge size for structures resembling a three-dimensional structure obtained by a researcher.

SUMMARY OF THE INVENTION

In view of the foregoing, an object of the present invention is to provide a method of searching a protein structure database with peripheral distributions of distance maps, where a protein structure, which is three-dimensional information, is converted into one-dimensional information called peripheral distribution and then subjected to a dynamic programming algorithm (DP). The method can realize high speed search with high detection sensitivity.

In order to achieve the above object, the present invention provides a method of searching a database of three-dimensional protein structures, comprising the steps of setting a three-dimensional protein structure; forming a two-dimensional distance map based on the three-dimensional protein structure; forming a one-dimensional peripheral distribution based on the distance map; and comparing the one-dimensional peripheral distribution with that for another three-dimensional protein structure by use of a dynamic programming algorithm.

Preferably, the distance map is a two dimensional image and has a structure of a triangular matrix in which respective columns or respective rows correspond to respective residues of a protein; the i-th row corresponds to the i-th amino acid residue counted from the N terminal end, and the j-th column corresponds to the j-th amino acid residue counted from the N terminal end; each element (i, j) of the matrix corresponds to the distance between the i carbon of the i-th residue and the x carbon of the j-th residue; and when the distance is smaller than or equal to a given threshold $r_0$, a dot is assigned to that portion, and when the distance is greater than the threshold $r_0$, a blank space is assigned to that portion, which operation is performed for each element in order to complete a binary distance map.

Preferably, the peripheral distribution is composed of a vertical peripheral distribution obtained in the form of a distribution of the frequency of dots at respective rows in a binary distance map and a horizontal peripheral distribution obtained in the form of a distribution of the frequency of dots at respective columns in the binary distance map.

Preferably, for comparison between peripheral distributions, an alignment score obtained by the dynamic programing algorithm is used as a similarity between corresponding protein structures.

A two-dimensional matrix, D, is required for the comparison of peripheral distributions. Each element of the matrix D is preferably obtained by solving the following recurrence equation:

$$D_{i,j} = \max\{D_{i-1,j-1} + s_{i,j}, D_{i-1,j} - g, D_{i,j-1} - g\}$$

where $S_{i,j}$ indicates the similarity between the i-th element of the peripheral distribution of protein A and the j-th element of the peripheral distribution of protein B; and g=5 : gap penalty (however, g=0 at the boundary)

Through the solution of the equation, the similarity is accumulated from the upper left corner toward the lower right corner of the matrix D, considering insertion and deletion. Then, the similarity between two peripheral distributions is obtained as a value for the element of the lower right corner of the matrix D.

$s_{i,j}$ is obtained by the following equation:

$$S_{i,j} = a/\{(N^A_i - N^B_j)^2 + b\} + a/\{(C^A_i - C^B_j)^2 + b\}$$

where $N^A_i$ indicates the j-th frequency of the vertical peripheral distribution of protein A;

$C^A_i$ indicates the i-th frequency of the horizontal distribution of protein A;

$N^B_j$ indicates the j-th frequencies of the vertical peripheral distributions of protein B;

$C^B_j$ indicates the j-th frequencies of the horizontal peripheral distribution of protein B; and where a=50, and b=2.

Preferably, a dot frequency R of a distance map is defined as follows:

R=number of dot elements in a distance map/total number of elements in the distance map; and the threshold is determined such that the dot frequency R falls within a predetermined range, and thus the detection sensitivity is increased.

More preferably, the threshold is determined such that the dot frequency R falls within the range of 0.12 to 0.16.

BRIEF DESCRIPTION OF THE DRAWINGS

FIG. 7 is an explanatory view showing a method of calculating the similarity between peripheral distributions according to the present invention;

FIG. 8 is a list of data used in measurement of the performance in a specific example of the present invention;

FIG. 10 is an explanatory view showing a method of evaluating the detection sensitivity;

FIG. 11 is a table showing the effect of the dot frequency R on the detection sensitivity;

FIG. 12 is a table showing the result of comparison between the present search method and the search method utilizing the DDP;

FIGS. 13(a) and 13(b) show an example of a structure database search in which β-lactoglobulin is used as a query structure;

FIGS. 14(a) and 14(b) show the result of a search in which heat shock protein 70 (HSP 70) is used as a query structure; and FIGS. 15(a) and 15(b) show the result of a search in which biotin carboxylase is used as a query structure.

DESCRIPTION OF THE PREFERRED EMBODIMENT

An embodiment of the present invention will next be described in detail with reference to the drawings.

Figure 1:
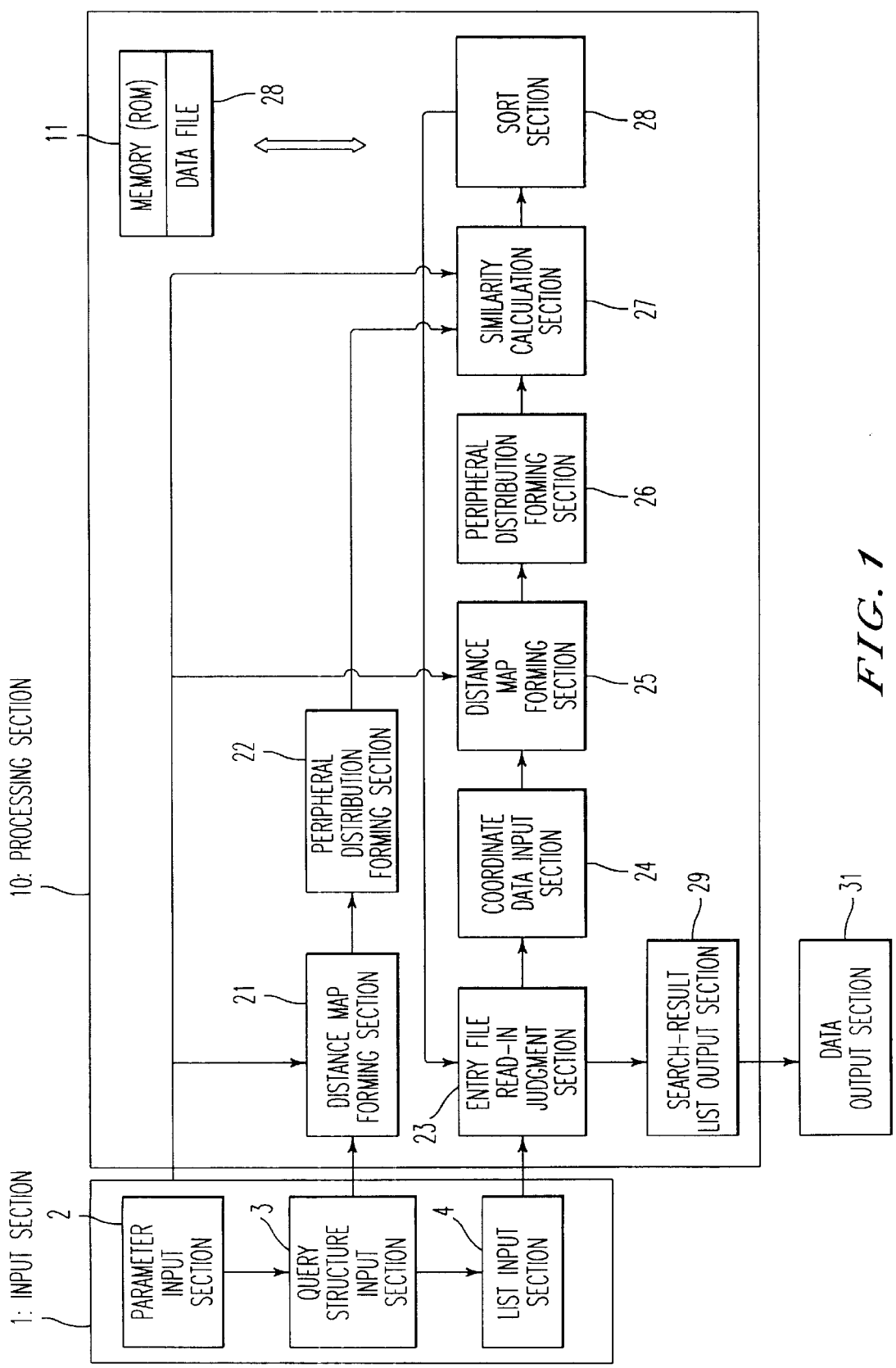
FIG. 1 is a diagram showing the structure of a database search system according to an embodiment of the present invention.
Figure 2:
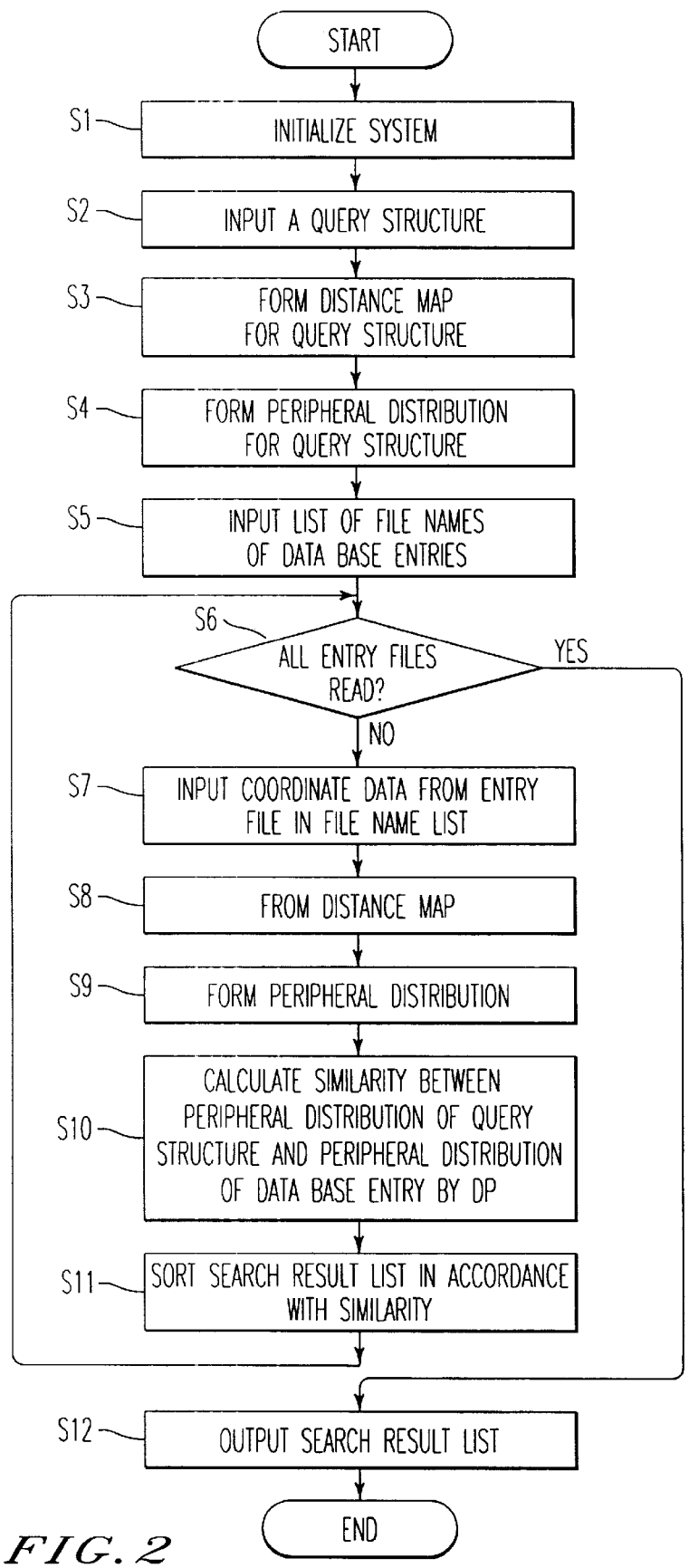
FIG. 2 shows a flowchart illustrating a search performed through use of the protein structure database search system of FIG. 1.

FIG. 1 shows the structure of a protein structure database search system according to an embodiment of the present invention; and FIG. 2 shows a flowchart illustrating a search performed through use of the protein structure database search system of FIG. 1.

In FIG. 1, numeral 1 denotes an input section, which includes a parameter input section 2, a query structure input section 3, and a list input section 4 for inputting a list of the file names of entry files of a database. Numeral 10 denotes a processing section, which includes a memory (ROM) 11 and a data file section 12. The memory 11 stores therein a program for controlling the overall system. The data file section 12 stores therein the list of the file names of entry files of the database, data of the query structure, parameter values, and the protein structure database.

The processing section 10 further comprises a first distance map forming section 21, a first peripheral distribution forming section 22, an entry file read-in judgment section 23, a coordinate data input section 24, a second distance map forming section 25, a second peripheral distribution forming section 26, a similarity calculation section 27, a sort section 28, a search-result list output section 29, and a data output section 31.

The parameter value input section 2 is applied to input parameters a, b, and g for the DP, as well as a threshold $r_0$ shown in FIG. 3, which will be described later. The threshold $r_0$ is used in the distance map forming sections 21 and 25, while values of the parameters a, b, and g are used in the calculation section 27.

The query structure input section 3 reads in coordinates of a query structure to be searched. For example, when the structure of one of the proteins shown in FIG. 8 is selected as a query structure to be searched, the coordinates of the structure corresponding to the selected protein are input.

The protein structure database is not a single file but is composed of a plurality of independent files of data regarding individual protein structures. The list input section 4 reads in only a list of the file names.

The entry file read-in judgment section 23 judges whether the entire database has been read.

The coordinate data input section 24 successively reads in structure data from the files of the database in accordance with the list input by the input section 4; i.e., the coordinate data input section 24 reads in one file at a time from the database, each file including the structure(s) of a protein(s).

The second distance map forming section 25 forms a distance map in accordance with the read-in structure data. The second peripheral distribution forming section 26 forms a peripheral distribution in accordance with the thus-obtained distance map.

The similarity calculation section 27 calculates similarity through comparison in which a peripheral distribution of a query structure is compared with a peripheral distribution of an entry of the database by use of the DP (dynamic programming).

On the basis of the thus-calculated similarity, the sort section 28 determines the position of a presently-handled entry of the structure database within a search result list calculated up to the present. That is, the sort section 28 sorts searched entries in accordance with similarity to the query structure.

Upon completion of read-in of all data in the structure database and the above-described calculation within the loop, searched entries of the structure database have been sorted in accordance with similarity to the query structure. The search result list output section 29 outputs the thus-obtained search result list.

Although a detailed description will be given hereinafter, a search performed through use of the above-described protein structure database search system will be described with reference to FIG. 2.

(1) First, the protein structure database search system is initialized (step S1). In this step, parameters, such as the threshold $r_0$ and parameters a, b, and g of the DP, are input.

(2) Subsequently, a query structure is input (step S2).

(3) A distance map for the query structure is formed (step S3).

(4) A peripheral distribution for the query structure is formed (step S4).

(5) Subsequently, a list of file names of entry files of the database is input (step S5).

(6) Next, a check is made as to whether all of the entry files have been read in (step S6).

(7) When the result of the judgment in step S4 is NO, coordinate data are obtained from an entry file within the file name list (step S7).

(8) Subsequently, a distance map is formed (step S8).

(9) Next, a peripheral distribution is formed (step S9).

(10) Subsequently, the similarity between a peripheral distribution of the query structure and the peripheral distribution of the database entry is calculated by means of the DP (step S10).

(11) Subsequently, sorting on the basis of the similarity is performed (step S11), and the processing proceeds back to step S4. The above-described procedure is repeated until all of the entry files are read in.

(12) When it is judged in step S4 that all of the entry files have been read in, a search result list is output (step S12).

Next, the method of searching the protein structure database will be described in detail.

In some techniques, the three-dimensional structure of a protein is converted into a distance map—which can be treated as a two-dimensional image—based on inter-residue distances and is displayed. As will be described later, when two proteins are similar in three-dimensional structure, their patterns on the respective distance maps are also similar to each other, even if their amino acid sequences differ. Accordingly, a protein having a similar structure can be found through comparison of distance maps.

Each distance map can be regarded or handled as a two-dimensional image. Pattern recognition of such a two-dimensional image is an important them to be studied in the field of computer vision. In the present invention, among the methods used for the pattern recognition of two-dimensional images, a classical peripheral distribution scheme is used in order to covert a distance map into one-dimensional information.

Figure 3:
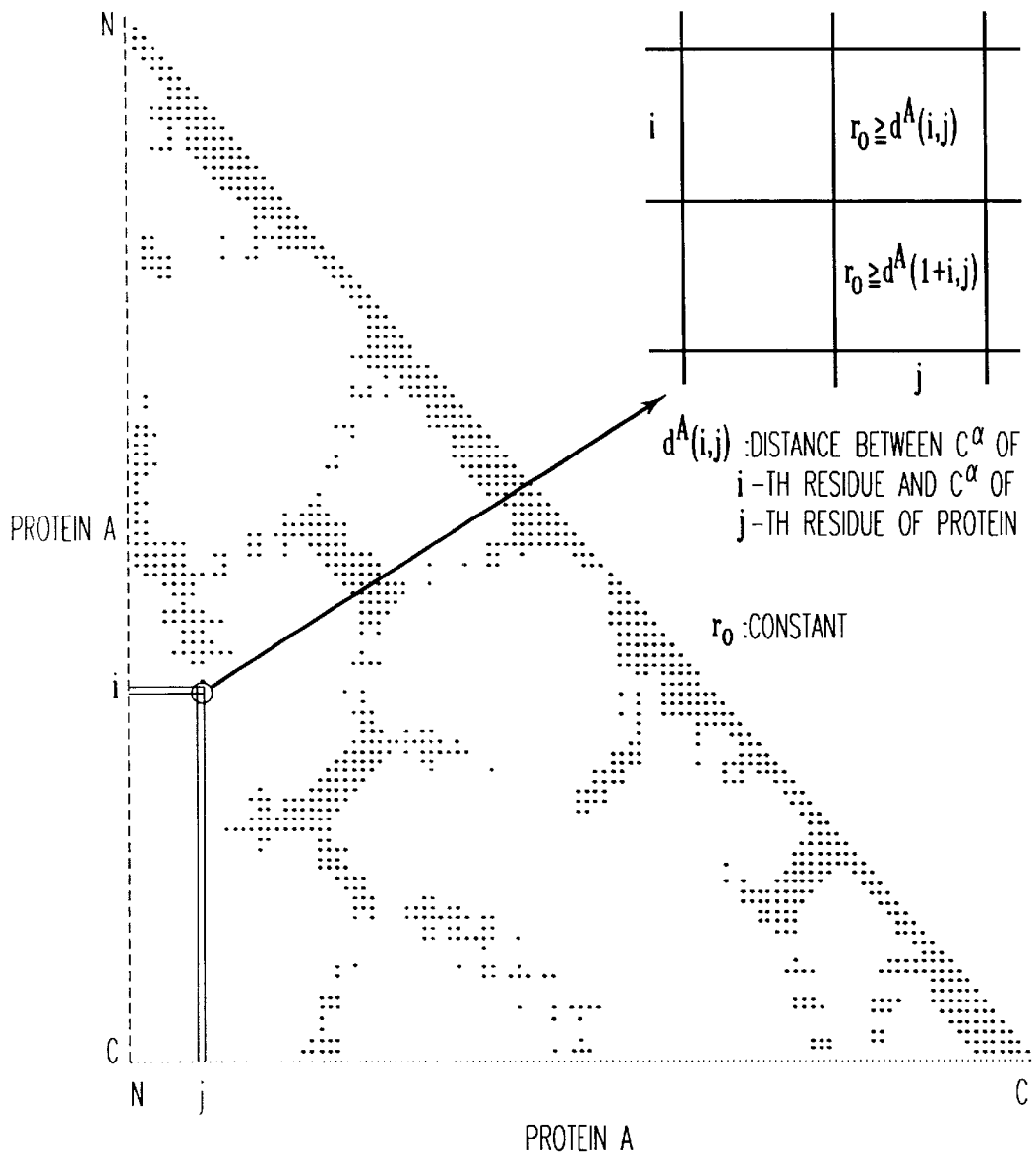
FIG. 3 is an explanatory view showing a method of forming a binary distance map in accordance with the embodiment of the present invention.

FIG. 3 shows a method of forming a binary distance map in accordance with the embodiment of the present invention.

The three-dimensional structure of a protein can be converted into a distance map, which is an two-dimensional image, through utilization of the distance between α carbons in residues thereof. In the present embodiment, a binary distance map is prepared in the following manner for conversion to a peripheral distribution.

The distance map has a structure of a triangular matrix, in which respective columns or respective rows correspond to respective residues of a protein. For example, the i-th row corresponds to the i-th amino acid residue counted from the N terminal end, and the j-th column corresponds to the j-th amino acid residue counted from the N terminal end. Each element (i, j) of the matrix corresponds to the distance between the a carbon of the i-th residue and the a carbon of the j-th residue. When the distance is smaller than or equal to a given threshold value (constant) $r_0$, a dot is assigned to that portion, and when the distance is greater than the threshold value $r_0$, a blank space is assigned to that portion. This operation is performed for each element in order to complete the distance map.

Next, there will be described comparison between distance maps.

Figure 4A:
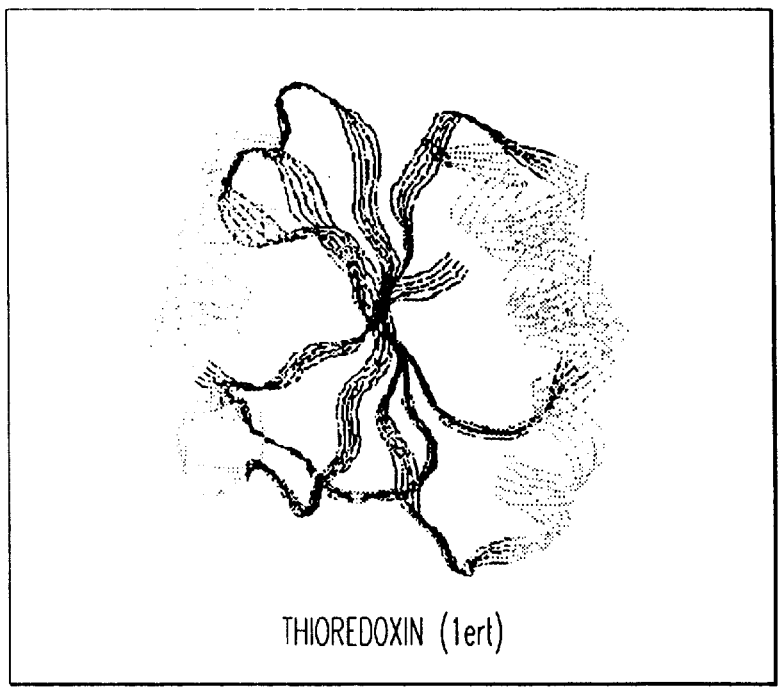
FIGS. 4(a) and 4(b) are diagrams each showing a three-dimensional structure of thioredoxin.
Figure 4B:
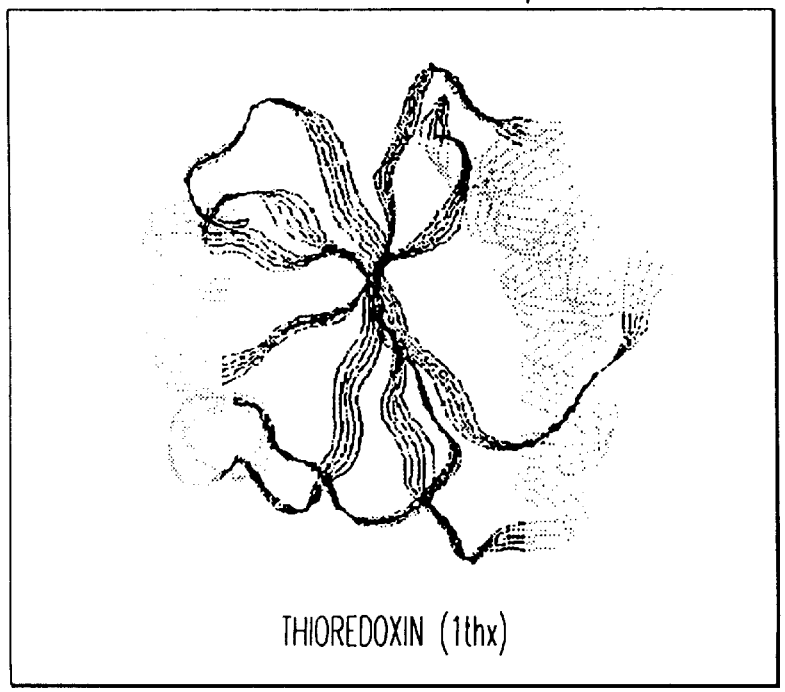

FIG. 4(a) is a view showing a three-dimensional structure of thioredoxin derived from humans, whereas FIG. 4(b) is a view showing a three-dimensional structure of thioredoxin derived from bacteria.

As shown in FIGS. 4(a) and 4(b), the human thioredoxin and the bacteria thioredoxin have similar three-dimensional structures, although their amino acid sequence identity is only 23.3%.

Figure 5A:
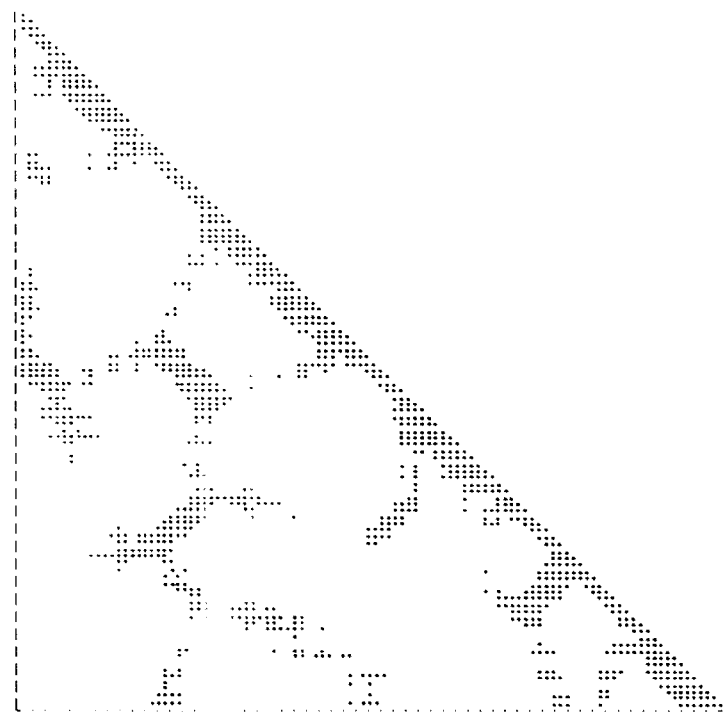
FIG. 5 is a diagram showing distance maps of thioredoxins shown in FIGS. 4(a) and 4(b)
Figure 5B:
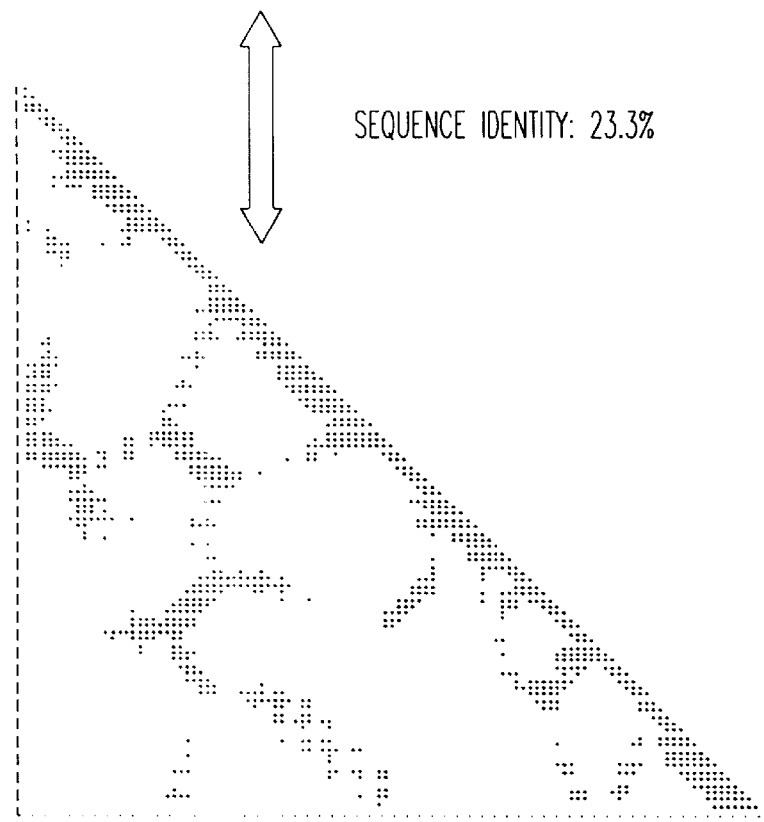

FIG. 5 shows distance maps which correspond to the two structures shown in FIGS. 4(a) and 4(b) and which are formed through the steps of FIG. 3. As shown in FIG. 4, the two structures are similar to each other, although the sequence identity is only 23.3%. Reflecting the structural similarity, the distance maps are similar to each other. Accordingly, similarity between the two structures is expected to be evaluated not through comparison of their three-dimensional structures but through comparison of patterns on their distance maps.

Next, formation of peripheral distribution will be described.

EIG. 6 is an explanatory view showing a method of forming a peripheral distribution.

First, a method of forming a peripheral distribution used in the field of character recognition is described.

Consider that a letter "A" is drawn on a plane. The plane is divided into small squares by a mesh, and each square is colored black or white (coded in binary form) in order to represent the letter "A." For each row, the black elements are counted so as to obtain a frequency of black elements for the row. This procedure is repeated for all the rows in order to obtain a vertical peripheral distribution V.

Figure 6A:
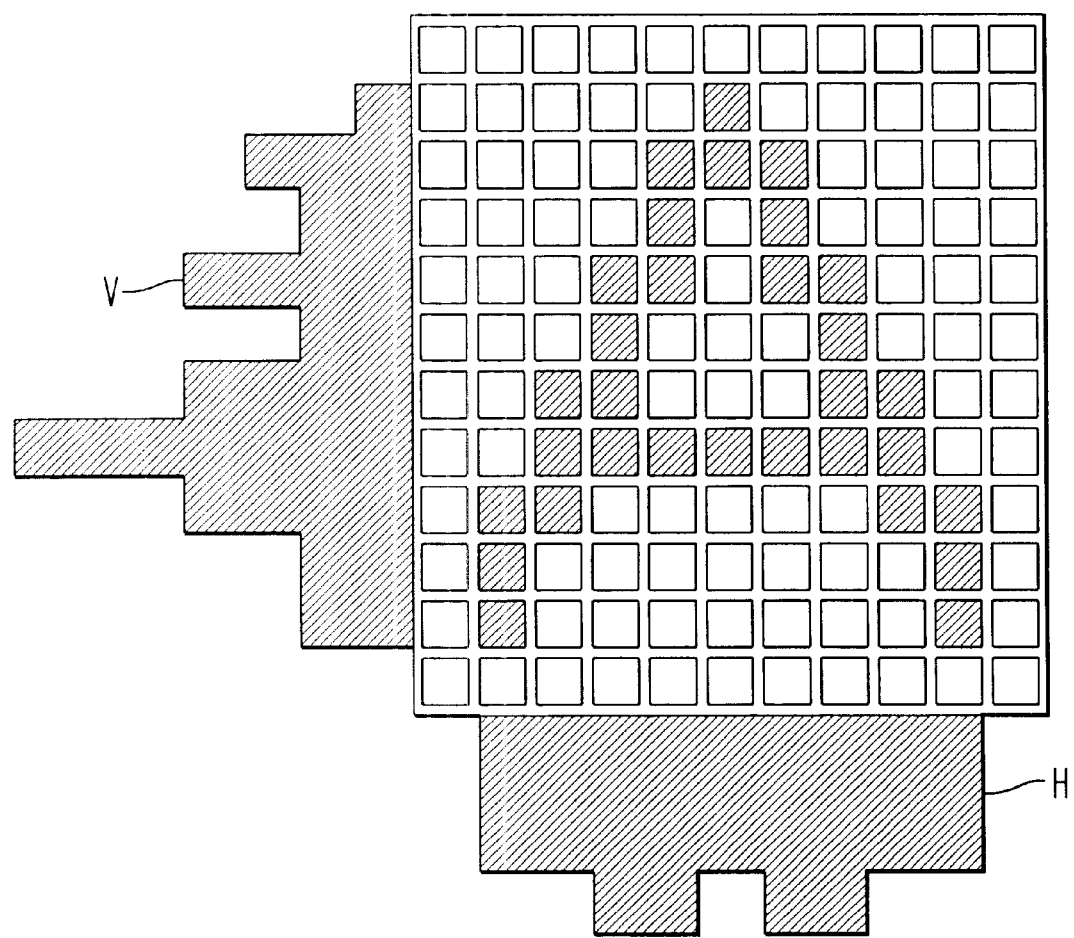
FIGS. 6(a) and 6(b) are explanatory views showing a method of forming a peripheral distribution.

A similar procedure is performed in order to obtain a horizontal peripheral distribution H. For example, the frequency of the third row in the vertical distribution is 3, since three black elements are present in the third row in the matrix of FIG. 6(a). The vertical and horizontal peripheral distributions are considered to represent the feature of the character "A." In the field of character recognition for printed Chinese characters, characters are recognized on the basis of such peripheral distributions.

Figure 6B:
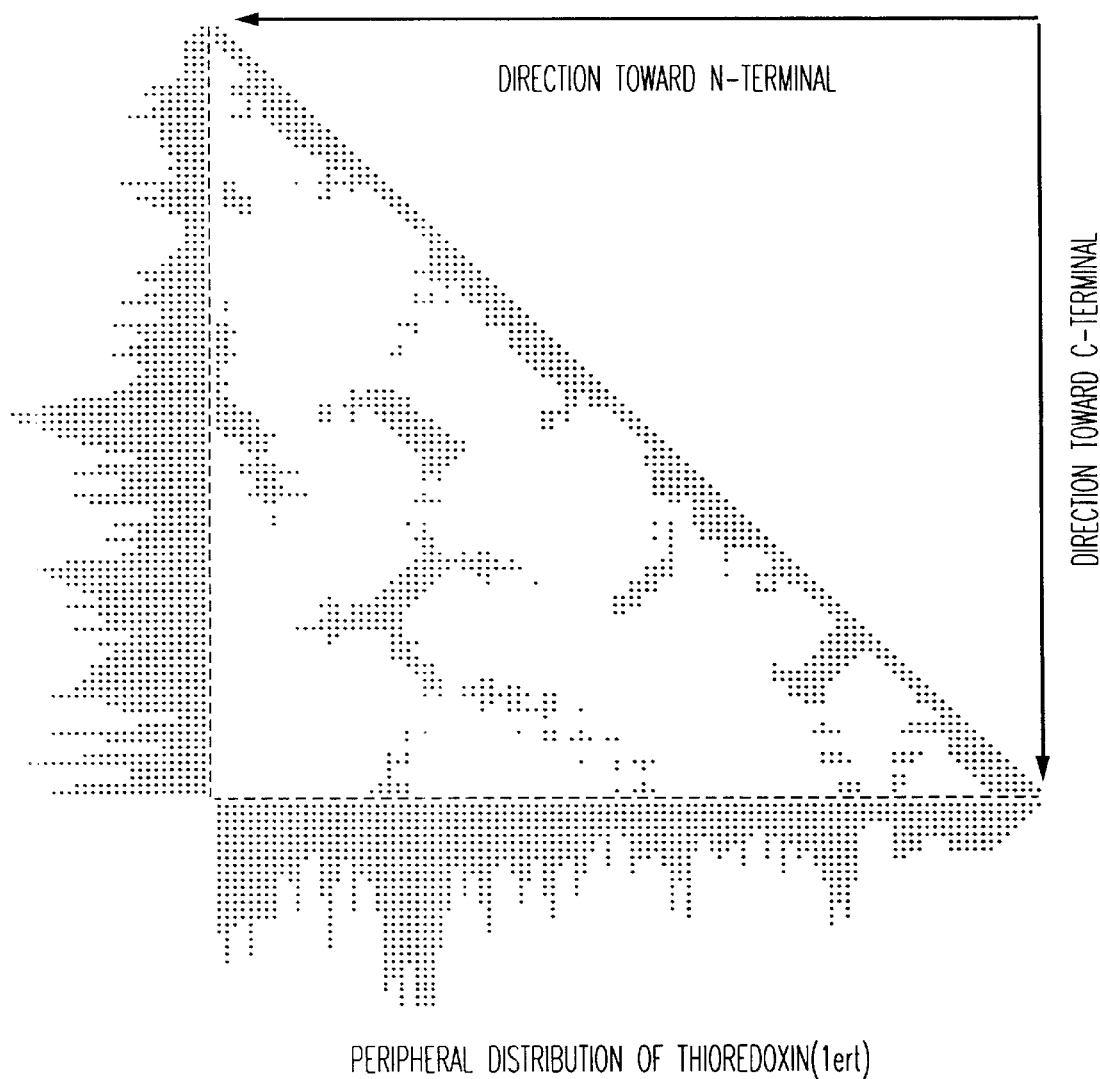

Since a distance map can be regarded as a two-dimensional image, vertical and horizontal peripheral distributions can be formed for the distance map according to a method similar to the method described above. FIG. 6(b) shows vertical and horizontal peripheral distributions formed by such a method. Via the distance map, which is two-dimensional information, the three-dimensional structure of a protein, which is three-dimensional information, can be converted into peripheral distributions, which are one-dimensional information.

As described above, the peripheral distributions of a distance map are considered to represent the characters of the distance map. Therefore, a similar structure can be recognized through comparison of peripheral distributions.

Next, there will be described methods of calculating the similarity between peripheral distributions.

First, there will be described a first method of calculating the similarity between peripheral distributions.

Character recognition is performed on the basis of similarity between peripheral distributions. The similarity is calculated through simple superimposition of the distributions or correlation of the Fourier spectrums of the distributions. However, neither method can deal with insertion or deletion, which occurs in proteins, but is not considered in ordinary character recognition.

In the technique for comparison of sequence data, an alignment score obtained as a result of a DP matching has been used as a similarity in which insertion and deletion are taken into consideration. Since peripheral distributions, like sequence data, are one-dimensional information, the present inventor tried to apply DP matching to peripheral distributions in a manner shown in FIG. 7.

FIG. 7 is an explanatory view showing a method of calculating the similarity between peripheral distributions according to the present invention.

In the DP for comparison of one-dimensional data, as shown in FIG. 7, a two-dimensional matrix, D, is required for the comparison of peripheral distributions. Each element of the matrix D is obtained by solving the following recurrence equation:

$$D_{i,j} = \max \{ ①D_{i-1,j-1} + s_{i,j}, ②D_{i-1,j} - g, ③D_{i,j-1} - g \}$$

where $s_{i,j}$ indicates the similarity between the i-th element of the peripheral distribution of protein A and the j-th element of the peripheral distribution of protein B; and g=5 : gap penalty (however, g=0 at the boundary)

Through the solution of the equation, the similarity is accumulated from the upper left corner toward the lower right corner of the matrix D, considering insertion and deletion. Then, the similarity between two peripheral distributions is obtained as a value for the element of the lower right corner of the matrix D.

$s_{i,j}$ is obtained by the following equation:

$$S_{i,j} = a/\{(N^A_i - N^B_j)^2 + b\} + a/\{(C^A_i - C^B_j)^2 + b\}$$

where $N^A_i$ indicates the j-th frequency of the vertical peripheral distribution of protein A;

$C^A_i$ indicates the i-th frequency of the horizontal distribution of protein A;

$N^B_j$ indicates the j-th frequencies of the vertical peripheral distributions of protein B;

$C^B_j$ indicates the j-th frequencies of the horizontal peripheral distribution of protein B; and where a=50, and b=2.

$S_{i,j}$ indicates the sum of the similarity in frequency of vertical distribution and the similarity in frequency of horizontal distributions between the i-th residue of protein A and the j-th residue of protein B. The similarity between two peripheral distributions is proportional to the size of the proteins corresponding to the distributions, even when the structures under comparison are not similar to each other.

To eliminate the size dependency, the similarity is divided by the length of aligned peripheral distributions by DP matching, which is used as the similarity between two structures.

Next, a specific example will be described.

The program is made by a program language, ANSI C. The performance of the system was evaluated on a computer, DEC Alpha Server $2100^{5/250}$. Protein Data Bank release #81 was used as the database for performance check, which is hereafter referred to as PDB.

Next, there is described data used in measurement of performance.

FIG. 8 shows data used in the measurement of performance in the specific example.

In order to investigate the sensitivity of the database search according to the present invention, the database search was performed with nine proteins having different structures in accordance with the method of the present invention, and the calculation time and detection sensitivity were measured.

The nine proteins having different structures were selected as follows.

First, in order to prevent the performance measurement for the method of the present invention from depending on the kinds of structures, three-dimensional structures were selected from each of three representative classes; i.e., mainly α, mainly β, and α/β.

Three kinds of proteins having different structures (categorized in different super families in accordance with the SCOP classification) were selected from each structural class, and search was performed. Then, nine proteins were used as query structures. FIG. 8 shows a list of the thus-selected nine proteins.

For comparison with the method of the present invention, database search with a double dynamic programming (DDP) method, which is a more precise structural comparison, as well as database search at the level of amino acid sequence, were performed with the nine proteins.

However, the search with the DDP was not performed for proteins having a size greater than 200 residues, because they required an excessively long time. The structural comparison with the DDP is disclosed in detail in Japanese Patent Application No. 8-340727, which was filed by the present inventor.

The database search at the level of amino acid sequence was performed with a program FASTA available at the internet site GenomeNet. Since this search was performed on a different computer, the calculation time is not shown.

Next, there will be described a dot frequency R, which is a factor for determining the detection sensitivity.

Figure 9:
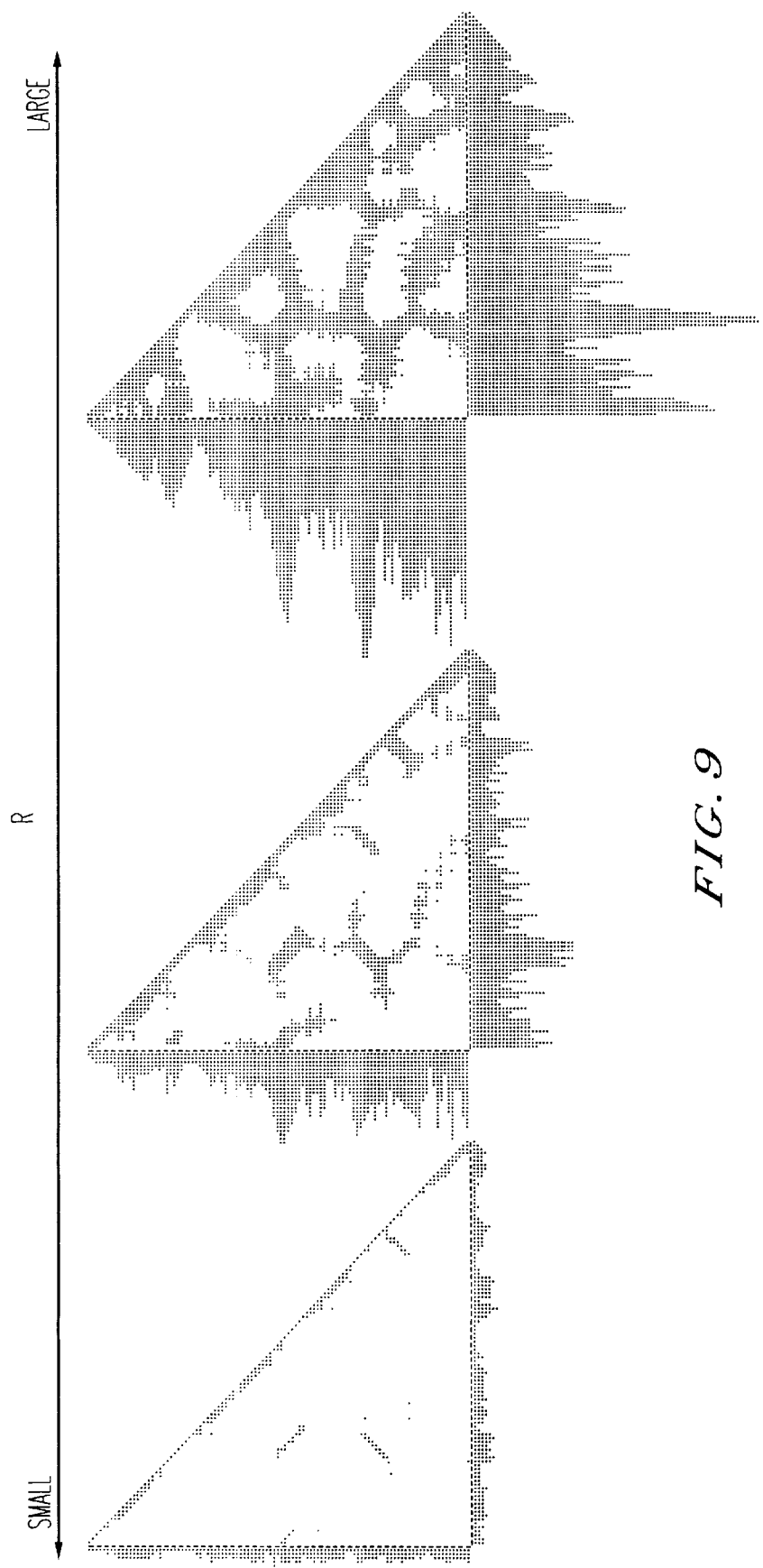
FIG. 9 is a diagram showing an effect of the dot frequency R on the search sensitivity.

FIG. 9 shows an effect of the dot frequency R on the detection sensitivity.

An attempt was made to set the threshold $r_0$ (see FIG. 3) for obtaining a binary distance map to an optimal value for database search. However, since the threshold $r_0$ for optimizing the detection sensitivity varied from protein to protein, the threshold $r_0$ could not be fixed to one value. The present inventor considered that, since the threshold $r_0$ is a factor that determines the frequency of dots in a distance map, the detection sensitivity is affected not by the threshold $r_0$ itself but by the dot frequency that is considered to relate to the characterization of the pattern of the distance map. Thus, the present inventor investigated the relationship between the dot frequency R and the detection sensitivity, while defining the dot frequency R as follows:

R=number of black elements of a distance map/total number of elements of the distance map.

As shown in FIG. 9, peripheral distribution characterizes the distance map or the tertiary structure when the dot frequency R is excessively small or excessively large.

Therefore, a proper value for the dot frequency R must be found.

The analysis described above reveals that a high detection sensitivity is obtained when the threshold $r_0$ is determined such that the dot frequency R falls within the range of 0.12 to 0.16.

The threshold $r_0$ that causes the dot frequency R to fall within the range described above varies from protein to protein.

FIG. 10 is an explanatory view to show a method of evaluating the detection accuracy.

In FIG. 10, symbol A denotes proteins that are categorized in a family in the SCOP (structure classification database) to which a query structure belongs; symbol B denotes proteins that are not categorized in the same family in the SCOP but are categorized in a class (superfamily) for proteins having structures that share the same topology in the structure with the query, but have weak similarity in amino acid sequence to the query; and proteins C (no symbol) are proteins classified into different superfamilies, to which a query structure does not belong.

As shown in FIG. 10, the names of entries in the database are output as a result of the search, in the form of a list where the entries are sorted in descending order of similarity to a query structure. In the test, it is needless to say that the entry at the top of the output list corresponds to the query structure itself, since each query structure is obtained from the entries of the structure database.

In the list, the members of class A or class B are regarded as "success." This process is repeated from the top of the list until a protein categorized in the class C is first found. The number (L) of proteins in the class A and the number (M) of proteins in the class B contained in the run of success are counted in order to calculate the ratio of the number L to the entire number of the class-A proteins of the structure data-base and the ratio of the number M to the entire number of the class-B proteins of the structure database. These ratios were used as indictors for detection sensitivity. Note that a class A or class B protein in the list is not counted for L or M if they do not belong to the run of success.

FIG. 11 is a table showing the effect of the dot frequency R on the detection sensitivity.

The first column shows the names of query structures. The fifth column shows the number of entries in the structure database classified into the classes A and B. The second to fourth columns respectively show the values of L and M for respective ranges for R. In each of the second to fifth columns, the number L of A-class proteins is shown on the left side of the "+" symbol, and the number M of B-class proteins is shown on the right side of the "+" symbol. When the value of R is less than 0.12 (second column), the sensitivity in detecting class-B proteins is extremely low, although most of the class-A proteins are detected for each query protein.

When the value of R is greater than 0.16 (fourth column), the sensitivity in detecting class-B proteins drops for some proteins, although class-A proteins are detected with high sensitivity. In contrast, when the value of R is greater than or equal to 0.12 and less than or equal to 0.16 (third column), the sensitivity in detecting class-B proteins is high.

The effect of the dot frequency R is shown for each of three structural classes; i.e., mainly α, mainly β, and α/β.

In FIG. 12, in order to demonstrate the performance of the method of the present invention, the result of database search according to the method of the present invention is compared with the result of database search according to the DDP previously proposed by the present inventor. Although structure comparison performed by the DDP is more precise than the method of the present invention, it takes a huge amount of time for calculation. As shown in FIG. 12, for class-A proteins, the search method of the present invention provides a detection sensitivity substantially equal to that obtained in the case of the search method utilizing the DDP. However, for class-B proteins, the search method of the present invention provides a detection sensitivity higher than that obtained in the case of the search method utilizing the DDP. Despite the higher sensitivity of current invention, the calculation time is greatly shortened compared to the case of the search method with the DDP. This demonstrates the superiority of the method of the present invention over the search method with the DDP, although the number of compared samples is small.

FIGS. 13(a) and 13(b) show an example of a structure database search in which β-lactoglobulin is used as a query structure. In FIGS. 13(a) and 13(b), a bar chart of frequency distribution of similarity is shown on the left side, an output list is shown on the right side.

β-lactoglobulin has a β-barrel structure with eight β strands and belongs to the lipocalin family. In the SCOP, the lipocalin and a family of proteins having a β-barrel structure with ten β strands form a superfamily in terms of structure.

In the present invention, class A is defined as the lipocalin family, and class B is defined as proteins with a β-barrel structure composed of ten β strands.

FIG. 13(a) shows the result of a search with the DDP. As shown in FIG. 12, the search with the DDP could not detect class-B proteins at all, although it could detect all of class-A proteins.

In contrast, as shown in FIG. 13(b), the search method of the present invention detected many class-B proteins after detection of all the class-A proteins. Although only the top fifty proteins are output, class-B proteins were detected after the run of success.

FIGS. 14(a) and 14(b) show the result of a search in which heat shock protein 70 (HSP 70) is used as a query structure.

In this study, HSP 70 forms a family, which is used as class A. In the SCOP, actin and hexokinase are included in its classification for superfamily level. These were defined to form class B. Since HSP 70 is a very large protein of about 400 residues in length, search with the DDP was difficult from the viewpoint of computation time.

Therefore, instead of the DDP, the FASTA of the GenomeNet was used for detabase search of HSP 70 at sequence level. FIG. 14(a) shows the result of search with the FASTA.

The FASTA could not detect any class-B proteins at all, although it could detect all of class-A proteins. In contrast, FIG. 14(b) shows the result of the search with the method of the present invention. As shown in FIG. 14(b), actin belonging to the class B was detected after detection of all the class-A proteins. However, hexokinase was not detected. The result of the FASTA demonstrates that, no significant similarity is observed at the sequence level, although HSP 70 and actin resemble each other in structure.

FIGS. 15(a) and 15(b) show the result of a search in which biotin carboxylase is used as a query structure.

Biotin carboxylases form one family by themselves, and therefore it was used as class A.

Although biotin carboxylase exhibits structural and functional similarity with D-Ala-D-Ala ligase and glutathione synthetase, no significant similarity is observed at the sequence level. Therefore, these were used as class B. Instead of the DDP, the FASTA of the GenomeNet was used for search and comparison, since biotin carboxylase is also a very large protein of about 400 residues in length. FIG. 15(a) shows the result of search with the FASTA. In this case, the FASTA could detect D-Ala-DAla ligases, as well as all of the class A proteins. However, no glutathione synthetase was detected. In contrast, as shown in FIG. 15(b), the method of the present invention could detect glutathione synthetases after detection of class A proteins and D-Ala-D-Ala ligase.

Further, many glutathione synthetases are found after the run of success in the output list. However, they are not taken into consideration in the evaluation method described above.

As is apparent from the specific example, the detection method of the present invention has a higher detection sensitivity than the DDP and FASTA.

The present invention is not limited to the embodiments described above. Numerous modifications and variations of the present invention are possible in light of the spirit of the present invention, and they are not excluded from the scope of the present invention.

As described above, according to the present invention, the three-dimensional structure of a protein, which is three-dimensional information, is converted into a peripheral distribution, which is one-dimensional information, and is then subjected to comparison with a dynamic programming algorithm. Therefore, the detection sensitivity can be increased, and high speed search can be realized.

Thus, a database search with high speed and high sensitivity was realized, which would cope with rapid increase of the entry of protein structure database to make enormous contribution to biology, pharmacology and physical chemistry.

What is claimed is:

1. A method of searching a database of three-dimensional protein structures, comprising the steps of:
    (a) setting a three-dimensional protein structure;
    (b) forming a two-dimensional binary distance map based on the three-dimensional protein structure;
    (c) forming a one-dimensional peripheral distribution based on the binary distance map; and
    (d) comparing the one-dimensional peripheral distribution with that for another three-dimensional protein structure by a dynamic programming algorithm.

2. A method of searching a database of three-dimensional protein structures according to claim 1, wherein said distance map is a two dimensional image and has a structure of a triangular matrix in which respective columns or respective rows correspond to respective residues of a protein; the i-th row corresponds to the i-th amino acid residue counted from the N terminal end, and the j-th column corresponds to the j-th amino acid residue counted from the N terminal end;

each element (i, j) of the matrix corresponds to the distance between the a carbon of the i-th residue and the a carbon of the j-th residue; and when the distance is smaller than or equal to a given threshold $r_0$, a dot is assigned to that portion, and when the distance is greater than the threshold $r_0$, a blank space is assigned to that portion, which operation is performed for each element in order to complete the binary distance map.

3. A method of searching a database of three-dimensional protein structures according to claim 2, wherein said peripheral distribution is composed of a vertical peripheral distribution obtained as a distribution of frequencies of dots at respective rows in a binary distance map and a horizontal peripheral distribution obtained as a distribution of frequencies of dots at respective columns in the binary distance map.

4. A method of searching a database of three .dimensional protein structures according to claim 3, wherein for comparison between peripheral distributions, an alignment score obtained by the dynamic programming algorithm divided by the alignment length is used as a similarity between two structures.

5. A method of searching a database of three-dimensional protein structures according to claim 3, wherein a two dimensional matrix, D, is used for the comparison of peripheral distributions; each element of the matrix D is obtained by solving the following recurrence equation; through the solution of the equation, the similarity is accumulated from the upper left corner toward the lower right corner of the matrix D, considering insertion and deletion; and then, the similarity between two peripheral distributions is obtained as a value for the element of the lower right of the matrix D:

$$D_{i,j} = \max \{D_{i-1, j-1} + s_{i, j}, D_{i-1, j} - g, D_{i, j-1} - g\}$$

where g=5 : gap penalty (however, g=0 at the boundary), and $S_{i, j}$ is represented by the following equation and indicates the similarity between the i-th element of the peripheral distribution of protein A and the j-th element of the peripheral distribution of protein B:

$$S_{i, j} = a/\{(N^A_i - N^B_j)^2 + b\} + a/\{(C^A_i - C^B_j)^2 + b\}$$

where $N^A_i$ indicates the j-th frequency of the vertical peripheral distribution of protein A;

$C^A_i$ indicates the i-th frequency of the horizontal distribution of protein A;

$N^B_j$ indicates the j-th frequencies of the vertical peripheral distributions of protein B;

$C^B_j$ indicates the j-th frequencies of the horizontal peripheral distribution of protein B; and a and b are constants.

6. A method of searching a database of three-dimensional protein structures according to claim 3, wherein a dot frequency R in the distance map is defined as follows:

R=number of black elements of a distance map/total number of elements of the distance map; and the threshold is determined such that the dot frequency R falls within a predetermined range, and the detection sensitivity is increased.

7. A method of searching a database of three dimensional protein structures according to claim 3, wherein the threshold is determined such that the dot frequency R falls within the range of 0.12 to 0.16.

* * * * *